United States Patent [19]

Halenbeck et al.

[11] Patent Number: 4,929,700

[45] Date of Patent: May 29, 1990

[54] PRODUCTION OF PURIFIED, BIOLOGICALLY ACTIVE, BACTERIALLY PRODUCED RECOMBINANT HUMAN CSF-1

[75] Inventors: Robert Halenbeck, San Rafael; Kriston Koths, El Cerrito; Cynthia Cowgill, Berkeley; Walter J. Laird, Pinole, all of Calif.

[73] Assignee: Cetus Corporation, Emeryville, Calif.

[21] Appl. No.: 173,428

[22] Filed: Apr. 8, 1988

Related U.S. Application Data

[63] Continuation-in-part of Ser. No. 114,001, Oct. 27, 1987, abandoned, which is a continuation-in-part of Ser. No. 40,174, Apr. 16, 1987, abandoned.

[51] Int. Cl.[5] .......... C07K 3/28

[52] U.S. Cl. .......... 530/351; 530/395; 530/404; 530/402; 530/405; 530/412; 530/413; 530/414; 530/415; 530/416; 530/416; 530/418; 530/419; 530/422; 530/820; 530/825; 435/69.5; 435/69.6; 435/71.2

[58] Field of Search .......... 530/395, 351, 412–419, 530/422, 402, 404–405; 435/68, 70

[56] References Cited

U.S. PATENT DOCUMENTS

| | | | |
|---|---|---|---|
| 4,338,397 | 7/1982 | Gilbert et al. | 435/68 |
| 4,411,994 | 10/1983 | Gilbert et al. | 435/71 |
| 4,464,295 | 8/1984 | Bhaduri et al. | 260/112 R |
| 4,476,049 | 10/1984 | Kung | 260/112 R |
| 4,511,502 | 4/1985 | Builder et al. | 260/112 R |
| 4,511,503 | 4/1985 | Olson et al. | 260/112 R |
| 4,512,922 | 4/1985 | Jones | 260/112 R |
| 4,518,526 | 5/1985 | Olson | 270/112 R |
| 4,530,787 | 7/1985 | Shaked et al. | 260/112 R |
| 4,569,790 | 2/1986 | Koths et al. | 260/112 R |
| 4,572,798 | 2/1986 | Koths et al. | 260/112 R |
| 4,599,197 | 7/1986 | Wetzel | 530/405 |
| 4,604,377 | 8/1986 | Fernandes et al. | 514/8 |
| 4,620,948 | 11/1986 | Builder et al. | 530/419 |
| 4,656,255 | 4/1987 | Seely | 530/412 |
| 4,659,568 | 4/1987 | Heilman, Jr. | 425/88 |
| 4,677,196 | 6/1987 | Rausch et al. | 530/412 |
| 4,711,843 | 12/1987 | Chang | 435/68 |
| 4,711,844 | 12/1987 | Chang | 435/317 |
| 4,748,234 | 5/1988 | Dorin et al. | 530/412 |
| 4,766,205 | 8/1988 | Ghosh-Dastidar | 530/402 |
| 4,766,224 | 8/1988 | Rausch | 530/412 |

FOREIGN PATENT DOCUMENTS

| | | |
|---|---|---|
| 4307085 | 12/1985 | Australia . |
| 114506 | 8/1984 | European Pat. Off. . |
| 0145390 | 6/1985 | European Pat. Off. . |
| 0147819 | 7/1985 | European Pat. Off. . |
| 0156373 | 10/1985 | European Pat. Off. . |
| 0185459 | 6/1986 | European Pat. Off. . |
| 0215625 | 8/1986 | European Pat. Off. . |
| 0196864 | 10/1986 | European Pat. Off. . |
| 0206828 | 12/1986 | European Pat. Off. . |
| 0208539 | 1/1987 | European Pat. Off. . |
| 0212960 | 3/1987 | European Pat. Off. . |
| 0218374 | 4/1987 | European Pat. Off. . |
| 0225156 | 6/1987 | European Pat. Off. . |
| 0272779 | 6/1988 | European Pat. Off. . |
| 0289267 | 11/1988 | European Pat. Off. . |
| 8505637 | 12/1985 | PCT Int'l Appl. . |
| 8604607 | 8/1986 | PCT Int'l Appl. . |
| 8605809 | 10/1986 | PCT Int'l Appl. . |
| 8606385 | 11/1986 | PCT Int'l Appl. . |
| 8706954 | 11/1987 | PCT Int'l Appl. . |
| 8808849 | 11/1988 | PCT Int'l Appl. . |
| 8808850 | 11/1988 | PCT Int'l Appl. . |

OTHER PUBLICATIONS

Ben-Auram et al., *PNAS* 82, 1985, p. 4486.

Kawasaki et al., *Nature* 230, 1985, pp. 291–296.

(List continued on next page.)

*Primary Examiner*—Garnette D. Draper

*Attorney, Agent, or Firm*—Lisabeth F. Murphy; Jane R. McLaughlin; Albert P. Halluin

[57] ABSTRACT

A process for recovering dimeric, biologically active CSF-1 from bacterially expressed recombinant CSF1 genes is described. The process comprises recovery of the solubilized monomeric form, followed by dimerization under refolding conditions and further purification of the dimer. Heterodimers may also be produced by this process.

41 Claims, 9 Drawing Sheets

OTHER PUBLICATIONS

Caraculo et al., *J. Exp. Med.* 166, 1987, pp. 1851–1860.
Shodkul et al., *Proc. Soc. Exp. Biol. Med.* 164, 1980, pp. 40–50.
Abbond et al., *Blood* 58(6) 1981, pp. 1150–1154.
Shilh et al., *Arch. Biochem. and Biophys.* 253(1) 1987, pp. 205–213.
BioRad Bulletin #1153.
Sofer et al., *Bio Technique,* Nov./Dec. 1983, pp. 198–203.
Metcalf et al., *Blood* 67(2) 1986, pp. 257–267.
Clark et al., *Science* 236, 1987, pp. 1229–1237.
Sieff, *J. Clin. Invest.* 79, 1987, pp. 1549–1557.
A. White et al., "Principles of Biochemistry, Fifth Edition", McGraw–Hill, Inc. (1973) pp. 136–137.
Fetrow, J., et al., *Biotechnology,* 6:167–171, (1988).
Weber, K. et al., 1971, *J. Biol. Chem.* 246:4504–4509.
Light, A. in *Biotechniques* 1985, 3:298–306.
Winkler, M. E., 1985, *Biotechnology* 3:990–999.
Hermann, R. et al., 1985, *Biochem.* 24:1817–1821.
Boss, M. A. et al., 1984, *Nucl. Acids Res.* 12:3791–3806.
Cabilly, S. et al., 1984, *Proc. Natl. Acad. Sci. USA* 81:3273–3277.
Pigiet, V. P. et al., 1986, Proc. Natl. Acad. Sci. USA 83:7643–7647.
Tietze, R., 1969, *Anal. Biochem.* 27:502.
Dexter, T. M., 1984, *Nature* 309:746.
Vadas, M. A., 1983, *J. Immunol.* 130:793.
Das, S. et al., 1982, *J. Biol. Chem.* 257:13679.
Kawasaki, E. S. et al., 1985, *Science* 230:292–296.
Ladner, M. B. et al., 1987, *The EMBOJ.* 6(9):2693–3698.
Wong, G. et al., 1987, *Science* 235:1504–1509.
Metcalf, D., 1970, *J. Cell. Physiol.* 76:89.
Remington's Pharmaceutical Sciences, Mack Publishing Co., Easton, Pa., Latest edition.
Moore, R. N. et al., 1983, *J. Immunol.* 131:2374–2378.
Prystowoky, M. et al., 1984, *Am. J. Pathol.* 114:149.
Kawaguchi, Y. et al., 1984, *J. Biotechnol.* 1:307–315.
Marston, F. A. O. et al., 1984, *Biotechnol.* 2:800–804.
Tsuji, T. et al., 1987, *Biochem* 26:3129–3134.
Means, G. E. et al., *Chem. Modif. of Proteins* Holden--Day, pp. 221–222.
Becker, T. et al., 1983, *Biotech. Advs.* 1:247–261.
Kleid, D. G. et al., 1983, Devel. in Indust. Microbiol. 25:317–325.
Jaenicke, R. et al., 1986, *Meth. in Enzymol.* 131:218–250.
Sofer, G. et al., 1984, BioTechnology 2:1035–1038.
Weir, M. Symposium on HPLC of Proteins, W. Germany, Oct. 1986.
Klausner, A., 1986, *Biotechnol.* 4:1041–43.
Hermann, R. E. 1983, *J. Biol. Chem.* 258:11014–11019.
Baldwin, R. L. et al., 1975, *Ann. Rev. Biochem.* pp. 453–475.

```
                             20                        40                        60                        80
AGTGAGGCTC GGCCCGGGGA AAGTGAAAGT TTGCCTGGGT CCTCTCGGCG CCAGAGCCGC TCTCCGCATC CCAGGACAGC

                            100                       120
GGTGCGGCCC TCGGCCGGGG CGCCCACTCC GCAGCAGCCA

                            140                       160                       180
GCGAGCGAGC GAGCGAGCGA GGGCGGCCGA CGCGCCCGGC CGGGACCCAG CTGCCCGT ATG ACC GCG CCG GGC GCC
                                                                Moi Thr Ala Pro Gly Ala
                                                                -32

 200                     220
GCC GGG CGC TGC CCT CCC ACG ACA TGG CTG GGC
Ala Gly Arg Cys Pro Pro Thr Thr Trp Leu Gly

             240                        260                     280
TCC CTG CTG TTG TTG GTC TGT CTC CTG GCG AGC AGG AGT ATC ACC GAG GAG GTG TCG GAG TAC TGT
Ser Leu Leu Leu Leu Val Cys Leu Leu Ala Ser Arg Ser Ile Thr Glu Glu Val Ser Glu Tyr Cys
                                                            1

    300                     320
AGC CAC ATG ATT GGG AGT GGA CAC CTG CAG TCT
Ser His Met Ile Gly Ser Gly His Leu Gln Ser

             340                    360                             380
CTG CAG CGG CTG ATT GAC AGT CAG ATG GAG ACC TCG TGC CAA ATT ACA TTT GAG TTT GTA GAC GAG
Leu Gln Arg Leu Ile Asp Ser Gln Met Glu Thr Ser Cys Gln Ile Thr Phe Glu Phe Val Asp Gln
    20                                                                              40
    400                     420
GAA CAG TTG AAA GAT CCA GTG TGC TAC CTT AAG
Glu Gln Leu Lys Asp Pro Val Cys Tyr Leu Lys

                 440                 460                         480
AAG GCA TTT CTC CTG GTA CAA TAC ATA ATG GAG GAC ACC ATG CGC TTC AGA GAT AAC ACC CCC AAT
Lys Ala Phe Leu Leu Val Gln Tyr Ile Met Glu Asp Thr Met Arg Phe Arg Asp Asn Thr Pro Asn
                            *   60
     500                         520
GCC ATC GCC ATT GTG CAG CTG CAG GAA CTC TCT
Ala Ile Ala Ile Val Gln Leu Gln Glu Leu Ser
                        80
```

FIG. 5-1

```
                        540                                     560                                     580
TTG AGG CTG AAG AGC TGC TTC ACC AAG GAT TAT GAA GAG CAT GAC AAG GCC TGC GTC CGA ACT TTC
Leu Arg Leu Lys Ser Cys Phe Thr Lys Asp Tyr Glu Glu His Asp Lys Ala Cys Val Arg Thr Phe
                                                            100

            600                                     620
TAT GAG ACA CCT CTC CAG TTG CTG GAG AAG GTC
Tyr Glu Thr Pro Leu Gln Leu Leu Glu Lys Val

                        640                                     660                                     680
AAG AAT GTC TTT AAT GAA ACA AAG AAT CTC CTT GAC AAG GAC TGG AAT ATT TTC AGC AAG AAC TGC
Lys Asn Val Phe Asn Glu Thr Lys Asn Leu Leu Asp Lys Asp Trp Asn Ile Phe Ser Lys Asn Cys
        120
        700                                 720
AAC AAC AGC TTT GCT GAA TGC TCC AGC CAA GGC
Asn Asn Ser Phe Ala Glu Cys Ser Ser Gln Gly
140
                            740                                     760                                     780
CAT GAG AGG CAG TCC GAG GGA TCC TCC AGC CCG CAG CTC CAG GAG TGT GTC TTC CAC CTG CTG GTG
His Glu Arg Gln Ser Glu Gly Ser Ser Ser Pro Gln Leu Gln Glu Ser Val Phe His Lue Leu Val
                                        160
                800                                     820
CCC AGT GTC ATC CTG GTC TTG CTG GCC GTC GGA
Pro Ser Val Ile Leu Val Leu Leu Ala Val Gly
                                180
                            840                                     860                                     880
GGG CTC TTG TTC TAC AGG TGG AGG CGG CGG AGC CAT CAA GAG CCT CAG AGA GCG GAT TCT CCC TTG
Gly Leu Leu Phe Tyr Arg Trp Arg Arg Arg Ser His Gln Glu Pro Gln Arg Ala Asp Ser Pro Leu
                                                                200
                900                                     920
GAG CAA CCA GAG GGC AGC CCC CTG ACT CAG GAT
Glu Gln Pro Glu Gly Ser Pro Leu Thr Gln Asp

                            940                                     960                                     980                                     1000
GAC AGA CAG GTG GAA CTG CCA GTG TAG AGGGAATTCTA AGACCCCTCA CCATCCTGGA CACACTCGTT TGTCAATGTC
Asp Arg Gln Val Glu Leu Pro Val
                220
                        1020
CCTCTGAAAA TGTGACGCC AGCCCCGGAC

        1040                1060                1080                1100
ACAGTACTCC AGATGTTGTC TGACCAGCTC AGAGAGAGTA CAGTGGGACT GTTACCTTCC TTGATATGGA CAGTATTCTT

        1120                1140
CTATTTGTGC AGATTAAGAT TGCATTAGTT TTTTTCTTAA
```

FIG.5-2

```
      1160                  1180                  1200                  1220
CAACTGCATC ATACTGTTGT CATATGTTGA GCCTGTGGTC TATTAAAACC CCTAGTTCCA TTTCCCATAA ACTTCTGTCA

      1240                  1260
AGCCAGACCA TCTCTACCCT GTACTTGGAC AACTTAACTT

      1280                  1300                  1320                  1340
TTTTAACCAA AGTGCAGTTT ATGTTCACCT TTGTTAAAGC CACCTTGTGG TTTCTGCCCA TCACCTGAAC CTACTGAAGT

      1360                  1380
TGTGTGAAAT CCTAATTCTG TCATCTCCGT AGCCCTCCCA

      1400                  1420                  1440                  1460
GTTGTGCCTC CTGCACATTG ATGAGTGCCT GCTGTTGTCT TTGCCCATGT TGTTGATGTA GCTGTGACCC TATTGTTCCT

      1480                  1150
CACCCCTGCC CCCCGCCAAC CCCAGCTGGC CCACCTCTTC

      1520                  1540                  1560                  1580
CCCCTCCCAC CCAAGCCCAC AGCCAGCCCA TCAGGAAGCC TTCCTGGCTT CTCCACAACC TTCTGACTGC TCTTTTCAGT

      1600                  1620
CATGCCCCTC CTGCTCTTTT GTATTTGGCT AATAGTATAT

      1640
CAATTTGCAC TT
```

FIG. 5-3

```
    CCCTGCTGTTGTTGGTCTGTCTCCTGGCGAGCAGGAGTATCACC ' 44
-14 LeuLeuLeuLeuValCysLeuLeuAlaSerArgSerIleThr

  1 GAGGAGGTGTCGGAGTACTGTAGCCACATGATTGGGAGTGGACACCTGCAGTCTCTGCAG 104
    GluGluValSerGluTyrCysSerHisMETIleGlySerGlyHisLeuGlnSerLeuGln

    CGGCTGATTGACAGTCAGATGGAGACCTCGTGCCAAATTACATTTGAGTTTGTAGACCAG 164
 21 ArgLeuIleAspSerGlnMETGluThrSerCysGlnIleThrPheGluPheValAspGln

    GAACAGTTGAAAGATCCAGTGTGCTACCTTAAGAAGGCATTTCTCCTGGTACAAGACATA 224
 41 GluGlnLeuLysAspProValCysTyrLeuLysLysAlaPheLeuLeuValGlnAspIle

    ATGGAGGACACCATGCGCTTCAGAGATAACACCCCCAATGCCATCGCCATTGTGCAGCTG 284
 61 METGluAspThrMETArgPheArgAspAsnThrProAsnAlaIleAlaIleValGlnLeu

    CAGGAACTCTCTTTGAGGCTGAAGAGCTGCTTCACCAAGGATTATGAAGAGCATGACAAG 344
 81 GlnGluLeuSerLeuArgLeuLysSerCysPheThrLysAspTyrGluGluHisAspLys

    GCCTGCGTCCGAACTTTCTATGAGACACCTCTCCAGTTGCTGGAGAAGGTCAAGAATGTC 404
101 AlaCysValArgThrPheTyrGluThrProLeuGlnLeuLeuGluLysValLysAsnVal

    TTTAATGAAACAAAGAATCTCCTTGACAAGGACTGGAATATTTTCAGCAAGAACTGCAAC 464
121 PheAsnGluThrLysAsnLeuLeuAspLysAspTrpAsnIlePheSerLysAsnCysAsn

    AACAGCTTTGCTGAATGCTCCAGCCAAGATGTGGTGACCAAGCCTGATTGCAACTGCCTG 524
141 AsnSerPheAlaGluCysSerSerGlnAspValValThrLysProAspCysAsnCysLeu

    TACCCCAAAGCCATCCCTAGCAGTGACCCGGCCTCTGTCTCCCCTCATCAGCCCCTCGCC 584
161 TyrProLysAlaIleProSerSerAspProAlaSerValSerProHisGlnProLeuAla

    CCCTCCATGGCCCCTGTGGCTGGCTTGACCTGGGAGGACTCTGAGGGAACTGAGGGCAGC 644
181 ProSerMETAlaProValAlaGlyLeuThrTrpGluAspSerGluGlyThrGlyGlySer

    TCCCTCTTGCCTGGTGAGCAGCCCCTGCACACAGTGGATCCAGGCAGTGCCAAGCAGCGG 704
201 SerLeuLeuProGlyGluGlnProLeuHisThrValAspProGlySerAlaLysGlnArg

    CCACCCAGGAGCACCTGCCAGAGCTTTGAGCCGCCAGAGACCCCAGTTGTCAAGGACAGC 764
221 ProProArgSerThrCysGlnSerPheGluProProGluThrProValValLysAspSer

    ACCATCGGTGGCTCACCACAGCCTCGCCCCTCTGTCGGGGCCTTCAACCCCGGGATGGAG 824
241 ThrIleGlyGlySerProGlnProArgProSerValGlyAlaPheAsnProGlyMETGlu

    GATATTCTTGACTCTGCAATGGGCACTAATTGGGTCCCAGAAGAAGCCTCTGGAGAGGCC 884
261 AspIleLeuAspSerAlaMETGlyThrAsnTrpValProGluGluAlaSerGlyGluAla

    AGTGAGATTCCCGTACCCCAAGGGACAGAGCTTTCCCCCTCCAGGCCAGGAGGGGGCAGC 944
281 SerGluIleProValProGlnGlyThrGluLeuSerProSerArgProGlyGlyGlySer

    ATGCAGACAGAGCCCGCCAGACCCAGCAACTTCCTCTCAGCATCTTCTCCACTCCCTGCA 1004
301 METGlnThrGluProAlaArgProSerAsnPheLeuSerAlaSerSerProLeuProAla

    TCAGCAAAGGGCCAACAGCCGGCAGATGTAACTGGTACAGCCTTGCCCAGGGTGGGCCCC 1064
321 SerAlaLysGlyGlnGlnProAlaAspValThrGlyThrAlaLeuProArgValGlyPro

    GTGAGGCCCACTGGCCAGGACTGGAATCACACCCCCCAGAAGACAGACCATCCATCTGCC 1124
341 ValArgProThrGlyGlnAspTrpAsnHisThrProGlnLysThrAspHisProSerAla

    CTGCTCAGAGACCCCCCGGAGCCAGGCTCTCCCAGGATCTCATCACTGCGCCCCCAGGGC 1184
361 LeuLeuArgAspProProGluProGlySerProArgIleSerSerLeuArgProGlnGly
```

FIG. 6-1

```
    CTCAGCAACCCCTCCACCCTCTCTGCTCAGCCACAGCTTTCCAGAAGCCACTCCTCGGGC 1244
381 LeuSerAsnProSerThrLeuSerAlaGlnProGlnLeuSerArgSerHisSerSerGly

    AGCGTGCTGCCCCTTGGGGAGCTGGAGGGCAGGAGGAGCACCAGGGATCGGAGGAGCCCC 1304
401 SerValLeuProLeuGlyGluLeuGluGlyArgArgSerThrArgAspArgArgSerPro

    GCAGAGCCAGAAGGAGGACCAGCAAGTGAAGGGGCAGCCAGGCCCCTGCCCCGTTTTAAC 1364
421 AlaGluProGluGlyGlyProAlaSerGluGlyAlaAlaArgProLeuProArgPheAsn

    TCCGTTCCTTTGACTGACACAGGCCATGAGAGGCAGTCCGAGGGATCCTCCAGCCCGCAG 1424
441 SerValProLeuThrAspThrGlyHisGluArgGlnSerGluGlySerSerSerProGln

    CTCCAGGAGTCTGTCTTCCACCTGCTGGTGCCCAGTGTCATCCTGGTCTTGCTGGCCGTC 1484
461 LeuGlnGluSerValPheHisLeuLeuValProSerValIleLeuValLeuLeuAlaVal

    GGAGGCCTCTTGTTCTACAGGTGGAGGCGGCGGAGCCATCAAGAGCCTCAGAGAGCGGAT 1544
481 GlyGlyLeuLeuPheTyrArgTrpArgArgArgSerHisGlnGluProGlnArgAlaAsp

    TCTCCCTTGGAGCAACCAGAGGGCAGCCCCCTGACTCAGGATGACAGACAGGTGGAACTG 1604
501 SerProLeuGluGlnProGluGlySerProLeuThrGlnAspAspArgGlnValGluLeu

    CCAGTGTAGAGGGAATTCTAAGACCCCTCACCATCCTGGACACACTCGTTTGTCAATGTC 1664
521 ProVal...

    CCTCTGAAAATGTGACGCCCAGCCCCGGACACAGTACTCCAGATGTTGTCTGACCAGCTC 1724
    AGAGAGAGTACAGTGGGACTGTTACCTTCCTTGATATGGACAGTATTCTTCTATTTGTGC 1784
    AGATTAAGATTGCATTAGTTTTTTCTTAACAACTGCATCATACTGTTGTCATATGTTGA 1844
    GCCTGTGGTCTATTAAAACCCCTAGTTCCATTTCCCATAAACTTCTGTCAAGCCAGACCA 1904
    TCTCTACCCTGTACTTGGACAACTTAACTTTTTAACCAAAGTGCAGTTTATGTTCACCT 1964
    TTGTTAAAGCCACCTTGTGGTTTCTGCCCATCACCTGAACCTACTGAAGTTGTGTGAAAT 2024
    CCTAATTCTGTCATCTCCGTAGCCCTCCCAGTTGTGCCTCCTGCACATTGATGAGTGCCT 2084
    GCTGTTGTCTTTGCCCATGTTGTTGATGTAGCTGTGACCCTATTGTTCCTCACCCCTGCC 2144
    CCCCGCCAACCCCAGCTGGCCCACCTCTTCCCCCTCCCACCCAAGCCCACAGCCAGCCCA 2204
    TCAGGAAGCCTTCCTGGCTTCTCCACAACCTTCTGACTGCTCTTTTCAGTCATGCCCCTC 2264
    CTGCTCTTTTGTATTTGGCTAATAGTATATCAATTTGC
```

FIG. 6-2

12% SDS-PAGE (COOMASSIE STAINED)

PRODUCTION OF PURIFIED, BIOLOGICALLY ACTIVE, BACTERIALLY PRODUCED RECOMBINANT HUMAN CSF-1

CROSS-REFERENCE TO RELATED APPLICATION

This is a continuation-in-part of U.S. Ser. No. 114,001, filed 27 Oct. 1987, which is a continuation-in-part of U.S. Ser. No. 040,174, filed 16 Apr. 1987 now abandoned.

TECHNICAL FIELD

The invention relates to processes for purification and refolding of bacterially produced recombinant proteins in forms having high specific biological activity. In particular, it concerns procedures which make possible the production of biologically active, dimeric forms of CSF-1 from bacterial hosts expressing genes encoding the monomer.

BACKGROUND ART

Colony stimulating factor-1 (CSF-1) is one of several proteins which are capable of stimulating colony formation by bone marrow cells plated in semisolid culture medium. CSF-1 is distinguished from other colony stimulating factors by virtue of its ability to stimulate these cells to become predominantly macrophage colonies. Other CSFs stimulate the production of colonies which consist of neutrophilic granulocytes and macrophages; predominantly neutrophilic granulocytes; or neutrophilic and eosinophilic granulocytes and macrophages. A review of these CSFs has been published by Dexter, T. M., *Nature* (1984) 309:746, and by Vadas, M. A., *J Immunol* (1983) 130:793. There is currently no routine in vivo assay which is known to be specific for CSF-1 activity.

The characteristics of native human CSF-1 are complex, and in fact it is not yet clear what form of CSF-1 is active in the human body. Soluble forms of naturally-produced CSF-1 have been purified to various degrees from human urine, mouse L-cells, cultured human pancreatic carcinoma (MIA PaCa) cells, and also from various human and mouse lung cell conditioned media, from human T-lymphoblast cells, and from human placental-conditioned medium. Many, if not all of the isolated native CSF-1 proteins appear to be glycosylated dimers, regardless of source. There is considerable variety in the molecular weights exhibited by the monomeric components of CSF-1, apparently the result of variations in C-terminal processing and/or the extent of glycosylation. For example, Western analysis shows that the CSF-1 secreted by the MIA PaCa cell line contains reduced monomers of approximately 26 and 30 kd, as well as 40, 48, and 70 kd forms. Other CSF-1 molecular weights have been reported. For example, the monomeric reduced form of CSF-1 isolated from human urine is reported to be of the relatively low molecular weight of 25 kd when isolated, and 14–17 kd when extensively deglycosylated in vitro (Das, S. and Stanley, E. R., *J Biol Chem* (1982) 257:13679).

The existence of "native-like" CSF-1 reference proteins is important because these proteins provide standards against which to compare the quality and biological activity of refolded recombinant forms of CSF-1. For this purpose, we have relied upon the soluble CSF-1 produced by the Mia PaCa cell line as well as properties of other highly purified CSF-1 molecules which have been described in the literature. The specific activity of these purified "native-like" reference proteins has typically fallen in the range of 4 to $10\times10^7$ units per mg (as measured by in vitro mouse bone marrow colony-forming assays).

CSF-1 has also been produced from recombinant DNA using two apparently related cDNA clones: (1) a "short" form which encodes a message which, when translated, produces a monomeric protein of 224 amino acids preceded by a 32-amino acid signal sequence (Kawasaki, E. S., et al, *Science* (1985) 230:292–296, and PCT WO86/04607, both of which are incorporated herein by reference); and (2) a "long" form, encoding a monomeric protein of 522 amino acids, also preceded by the 32-amino acid signal sequence. The long form has been cloned and expressed by two groups, as disclosed in Ladner, M. B., et al, *The EMBO J* (1987) 6(9):2693–2698, and Wong, G., et al, *Science* (1987) 235:1504–1509, both of which are incorporated herein by reference. (The DNA and amino acid sequences for both "short" and "long" forms are shown in FIGS. 5 and 6, respectively; however, the 32 amino acid signal sequence is incomplete as illustrated in FIG. 6.)

The long and short forms of the CSF-1-encoding DNA appear to arise from a variable splice junction at the upstream portion of exon 6 of the genomic CSF-1-encoding DNA. When CSF-1 is expressed in certain eucaryotic cells from either the long or short cDNA forms, it appears to be variably processed at the C-terminus and/or variably glycosylated. Consequently, CSF-1 proteins of varying molecular weights are found when the reduced monomeric form is analyzed by Western analysis.

The amino acid sequences of the long and short forms, as predicted from the DNA sequence of the isolated clones and by their relationship to the genomic sequence, are identical with respect to the first 149 amino acids at the N-terminus of the mature protein, and diverge thereafter by virtue of the inclusion in the longer clone of an additional 894 bp insert encoding 298 additional amino acids following glutamine 149. Both the shorter and longer forms of the gene allow expression of proteins with sequences containing identical regions at the C-terminus, as well as at the N-terminus. Biologically active CSF-1 has been recovered when cDNA encoding through the first 150 or 158 amino acids of the short form, or through the first 221 amino acids of the longer form, is expressed in eucaryotic cells.

Since most, if not all, of the native secreted CSF-1 molecules are glycosylated and dimeric, significant posttranslational processing apparently occurs in vivo. Given the complexity of the native CSF-1 molecule, it has been considered expedient to express the CSF-1 gene in cells derived from higher organisms. It seemed unlikely that active protein would be obtained when the gene was expressed in more convenient bacterial hosts, such as *E. coli.* Bacterial hosts do not have the capacity to glycosylate proteins, nor are their intracellular conditions conducive to the refolding, disulfide bond formation, and disulfide-stabilized dimerization which is apparently essential for full CSF-1 activity. Thus, experimental production of recombinant CSF-1 in *E. coli* has, prior to this invention, resulted in protein of very low activity, although its identification as monomeric CSF-1 had been readily confirmed by immunoassay, N-terminal sequencing, and amino acid analysis.

It is by now accepted that inactive forms of recombinant foreign proteins produced in bacteria may require further "refolding" steps in order to render them useful for the purposes for which they are intended. As a dimeric protein containing a large number of cysteines and disulfide bonds, which are required for activity, CSF-1 represents a particularly difficult challenge for production from bacterial systems. Often, recombinant proteins produced in *E. coli,* including CSF-1 so produced, are in the form of highly insoluble intracellular protein precipitates referred to as inclusion bodies or refractile bodies. These inclusions can readily be separated from the soluble bacterial proteins, but then must be solubilized under conditions which result in essentially complete denaturation of the protein. Even secreted proteins from bacterial sources, while not necessarily presenting the same solubility problems, may require considerable manipulation in order to restore activity. Each different protein may require a different refolding protocol in order to achieve full biological activity.

A number of papers have appeared which report refolding attempts for individual proteins produced in bacterial hosts, or which are otherwise in denatured or non-native form. A representative sample follows.

Reformation of an oligomeric enzyme after denaturation by sodium dodecyl sulfate (SDS) was reported by Weber, K., et al, *J Biol Chem* (1971) 246:4504–4509. This procedure was considered to solve a problem created by the binding of proteins to SDS, and the process employed removal of the denatured protein from SDS in the presence of 6M urea, along with anion exchange to remove the SDS, followed by dilution from urea, all in the presence of reducing agents. The proteins which were at least partially refolded included: aspartate transcarbamylase, B-galactosidase, rabbit muscle aldolase, and coat protein from bacteriophage R-17.

Light, A., in *Biotechnicues* (1985) 3:298–306, describes a variety of attempts to refold a large number of proteins. It is apparent from the description in this reference that the techniques which are applicable are highly individual to the particular protein concerned. In fact, in some cases, refolding significant amounts of particular proteins has not been possible and the results are quite unpredictable. In addition, refolding procedures for recombinant urokinase produced in *E. coli* were described in Winkler, M. E., *Biotechnology* (1985) 3:990–999. In this case, the material was dissolved in 8M urea or 5M guanidine hydrochloride, and the rearrangement of disulfides was facilitated by use of a buffer containing a glutathione redox system. Recombinant human immune interferon, which has no disulfide bonds, has been refolded to generate a more active preparation using chaotropic agents in the absence of thiol-disulfide exchange reagents (PCT application WO 86/06385). In another example, bacterially synthesized granulocyte macrophage colony-stimulating factor (GM-CSF), a member of the CSF group, was also produced in *E. coli* and refolded after solubilization in 6M urea. This CSF is unrelated to CSF-1, since GM-CSF has a distinct amino acid sequence and is also monomeric.

Use of refolding procedures to obtain reconstitution of activity in multimeric proteins has also been described by Herman, R. H., et al, *Biochemistry* (1985) 24:1817–1821, for phosphoglycerate mutase, and by Cabilly, S., *Proc Natl Acad Sci USA* (1984) 81:3273–3277, for immunoglobulins. An additional procedure for immunoglobulin reassembly was described by Boss, M. A., et al, *Nucleic Acids Research* (1984) 12:3791–3806. These procedures all employ denaturation and the use of appropriate oxidizing and reducing agents or sulfitolysis reagents. A related approach employs the catalyst thioredoxin, and is disclosed by Pigiet, V. P., *Proc Natl Acad Sci USA* (1986) 83:7643–7647.

Certain aspects of solubilization, purification, and refolding of certain recombinant proteins produced as refractile bodies in bacteria are also disclosed in U.S. Pat. Nos. 4,511,502; 4,511,503; 4,512,922; 4,518,526 and EPO publication 114,506 (Genentech).

The foregoing references are merely representative of a large body of literature which, when taken together, shows individual steps in protocols which may be modified and combined in various sequences to obtain individually tailored procedures for particular subject proteins produced in accordance with particular expression systems. It is evident that retailoring of the overall procedures to fit a specific case is a requirement for producing refolded product with full biological activity in useful amounts.

For example, a number of the published procedures describe a step for successful refolding of the recombinantly produced protein. It is not clear from these references, but is known in the art, that the starting material for refolding may exist in a variety of forms, depending on the nature of the expression system used. In the case of bacterial expression, it is, however, clear that the product is not glycosylated, and that, in addition, production of an intracellular disulfide-bonded dimeric product is essentially prevented by the reducing environment in bacterial cells.

Currently the most common form of recombinant protein starting material for refolding is an intracellular, insoluble protein which is produced by expression of a gene for mature or bacterial fusion protein, lacking a functional signal sequence, under the control of standard bacterial promoters such as TRP or $P_L$. Because recombinantly produced products in bacteria are produced in high concentrations in a reducing environment, and because typically the constructs do not enable the bacteria to secrete the recombinant protein, these foreign proteins are often observed to form insoluble inclusion bodies.

However, signal sequences which function in bacteria are known, including the *E. coli* penicillinase sequence disclosed by Gilbert et al, U.S. Pat. Nos. 4,411,994 and 4,338,397, the *B. licheniformis* penP sequences disclosed by Chang in U.S. Patent Nos. 4,711,843 and 4,711,844, and the phosphatase A signal sequence (phoA) disclosed by Chang, et al, in European Patent Publication No. 196,864, published 8 Oct. 1986, and incorporated herein by reference. Secretion can be effected in some strains. However, if Gram-negative hosts are used, complete secretion may not occur, and the protein may reside in the periplasmic space. Nevertheless, it is much more likely that proteins expressed under control of promoters and signal sequences such as phoA will be produced in soluble form if they are capable of refolding and forming required disulfide bonds in the extracellular environment. The methods disclosed hereinbelow are expected to be of value for both intracellular and secreted products where refolding is required.

Nowhere in the literature is a specific process described for the preparation of biologically active dimeric CSF-1 from bacteria. The present invention describes several refolding procedures involving CSF-1 proteins of various primary structures. The resulting refolded CSF-1 proteins are fully active and soluble, and the various molecules differ sufficiently in physical properties that they may be expected to exhibit a variety of pharmacokinetic and/or pharmacological properties when used therapeutically in vivo.

DISCLOSURE OF THE INVENTION

The invention is directed to a procedure for assembly of biologically active, dimeric CSF-1 using the monomeric starting material produced by bacterial cells that have been transformed with suitable CSF-1 gene constructions. The procedure takes advantage of the different properties of the monomeric and dimeric forms of the protein to effect useful purification procedures, and employs suitable reagents to convert the insoluble monomeric form to an active, soluble, dimeric form.

Thus, in one aspect, the invention is directed to a method to obtain purified, biologically active CSF-1 dimer from the reduced monomeric product of the CSF-1 gene recombinantly expressed in bacteria. First, semipurified solubilized reduced monomer is maintained under reducing conditions to assure uniform starting material. Second, refolding of the monomer and association into dimer is conducted under suitable refolding conditions. Third, the refolded, dimeric CSF-1 is purified to remove contaminating proteins and endotoxins, yielding a product suitable for clinical use. In one embodiment, the process includes the step of solubilizing the recombinantly produced CSF-1; in other embodiments, the solubilized CSF-1 is subjected to a purification step before refolding.

In another aspect, the invention relates to a process of forming heterodimeric CSF-1 proteins from a mixture of different monomeric forms. The monomers may be mixed directly or may be mixed by virtue of production by the same recombinant cell. Such heterodimers may allow the production of CSF-1 products with improved in vivo utility.

Still another aspect includes the further step, if needed, of resolubilizing the residual insoluble CSF-1 present at the end of the refolding process and increasing yield through recycling.

In still another aspect, the invention relates to a process for obtaining clinically pure CSF-1 dimeric protein which comprises subjecting the refolded dimeric protein to chromatography using a hydrophobic support, such as phenyl-Sepharose or phenyl-TSK HPLC.

The invention, in other aspects, also is directed to the products of the foregoing processes, and specifically is directed to refolded, clinically pure, essentially endotoxin/pyrogen-free dimeric CSF-1 produced by expression in bacteria.

BRIEF DESCRIPTION OF THE DRAWINGS

FIG. 5 shows the cDNA and deduced amino acid sequence for a cDNA clone encoding a "short" form of human CSF-1 designated pcCSF-17.

FIG. 6 shows the cDNA and deduced amino acid sequence for a cDNA clone encoding a "long" form of human CSF-1 designated pcCSF-4.

MODES OF CARRYING OUT THE INVENTION

A. Definitions

Figure 1:
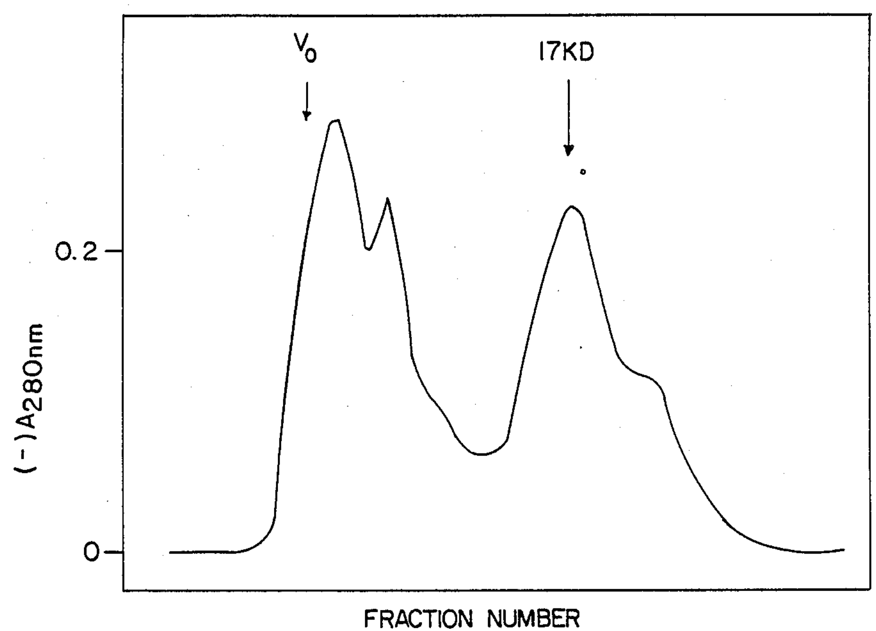
FIG. 1 shows the partial purification of one type of monomeric CSF-1 using molecular sieve chromatography.

As used herein, "chaotropic environment" refers to an environment which contains appropriate chaotropic agents, such as urea in sufficient concentration to disrupt the tertiary structure of proteins, or which is maintained at a temperature or other condition which causes such disruption. Chaotropic agents or conditions such as temperature and pH may disrupt structure in a variety of ways, including the disruption of hydrogen bonds. Suitable chaotropic environments include 2–8 M urea, 4–7 M guanidinium, detergents such as SDS at concentrations around 0.1% by weight, and acids such as acetic acid at concentrations of about 1 M, basic conditions of, e.g., pH 11 and above, and elevated temperatures. When placed in a chaotropic environment, the normal physiological conformation of proteins may be reversibly as well as irreversibly altered, and the primary structure may be "unfolded" to varying degrees, depending on the concentration of the chaotropic agent and the degree of severity of other chaotropic conditions. It should be understood that agents and/or conditions which create chaotropic environments can be used in combination or in sequence. For example, mixtures of chaotropic agents can be used, or the CSF-1 may first be placed in a chaotropic environment created by one chaotropic agent, and then subjected to a second chaotropic environment created by another agent or by temperature.

As used herein, "reducing agent" specifically refers to a reducing agent which is capable of reducing disulfide linkages to sulfhydryl groups. A variety of mildly reducing materials capable of effecting this conversion is available, but the most common comprises thiol-containing moieties such as β-mercaptoethanol or dithiothreitol. Additional functional reducing agents include reduced glutathione and free cysteine itself. While emphasis is placed on thiol-containing compounds, any material which is capable of the disulfide to thiol conversion without undesirable side reactions is included in this definition.

"Reducing conditions" refers to conditions which maintain or place, as the case may be, the CSF-1 protein in the monomeric reduced form. If the CSF-1 is produced in an environment which places it initially in reduced form (i.e., the cysteines are in said form, not cystine) milder conditions may suffice than would be required if the protein were initially in oxidized form.

"Refolding conditions" refers to conditions wherein a denatured protein is permitted to assume a conformation associated with physiological activity. This specifically includes formation of disulfides and/or association into dimeric or multimeric structures which are functionally identical to those of the native protein. Such conditions include slow removal of or step-wise dilution of chaotropic agents in the presence or absence of agents which permit the formation of disulfide bonds normally present in the active conformation. If high concentrations of chaotropic agents are used for solubilization, or if the protein is otherwise denatured by virtue of these agents, the chaotropic substances included in the chaotrope may be removed by simple dilution, by dialysis, by hollow fiber diafiltration, or by a number of other means known in the art by which the concentration of small molecules may effectively be lowered, with or without a corresponding decrease in the concentration of the protein.

It is desirable to promote disulfide bond formation during this process. This can be accomplished by air oxidation or by including reagents suitable for this purpose in the refolding conditions. Such reagents include "redox systems" which permit the continuous oxidation and reduction of the thiol/disulfide pairs. One of the most commonly used of these systems is glutathione, in both oxidized and reduced forms. It is known that oxidized glutathione and reduced glutathione are naturally occurring constituents of mammalian cells and may, in fact, in addition to or in conjunction with isomerases catalyzing this reaction, promote thiol/disulfide bond exchange in vivo (Tietze, F., *Anal Biochem* (1969) 27:502). Other pairs of oxidized (disulfide) and reduced (thiol) reagents may also be used; indeed, the disulfide and thiol need not be derived from the same molecule. In addition, new disulfide bonds may be formed by sulfitolysis, followed by oxidation of the sulfonated thiol groups. This process is described in U.S. Pat. No. 4,620,948 to Builder et al, supra.

The purification methods referred to herein include a variety of procedures. Among several types which may be useful are size fractionation using molecular sieve chromatography; ion-exchange chromatography under suitable conditions; affinity chromatography using, for example, monoclonal antibodies directed to the biologically active form of the protein; adsorption chromatography using nonspecific supports, such as hydroxyapatite, silica, alumina, and so forth; and also gel-supported electrophoresis. In the case of CSF-1, hydrophobic interaction chromatography, such as using phenyl-Sepharose or phenyl-TSK, has been shown to be particularly useful. In addition, initial purification of monomeric CSF-1 using ion-exchange chromatography (such as DEAE-Sepharose chromatography) has been shown to be a particularly effective procedure to increase the purity of the dimeric CSF-1 protein. These purification techniques are, in a general sense, well known in the art, and a detailed description of the pecularities of their specific application to CSF-1 proteins is described in the examples below.

As used herein, "biologically active" means a preparation of human CSF-1 produced recombinantly in bacteria which has essentially the same specific activity in human and mouse bone marrow colony-forming assays as native human CSF-1 produced by mammalian cells.

"Clinically pure" CSF-1 means a preparation of biologically active human CSF-1 produced recombinantly in bacteria which is at least 95% CSF-1 either by RP-HPLC or by either reducing or non-reducing SDS-PAGE and has an endotoxin content of less than about 1.0 ng/mg CSF-1 as assayed by standard LAL assay.

B. CSF-1 Proteins

As set forth in the background section, CSF-1 is biologically active in its dimeric form. It has been possible to obtain recombinant DNA encoding CSF-1 monomers consisting of a variety of amino acid sequences and lengths. FIGS. 5 and 6, respectively, show the DNA and amino acid sequences for the short and long forms, both of which may be preceded by a 32-amino acid signal sequence. The sequences of monomeric CSF-1 protein are considered herein for convenience to be the 224-amino-acid short form (SCSF) and the 522-amino-acid long form (LCSF) shown in these figures.

Plasmids encoding a variety of CSF-1 forms are currently available, and can be expressed in bacterial systems. As described immediately above, the gene encoding the long form of CSF-1 can be expressed in its entirety, or the gene can be truncated to express C-terminally deleted forms. In addition, the first two or three N-terminal codons can be deleted so that the resulting protein is more homogeneous. Specifically, the N-terminal methionine encoded upstream of the mature native sequence N-terminus (which is retained in the protein as "N-terminal Met" unless removed by post-translational processing), has been found to be more readily removed from these N-terminal deletion constructs. Furthermore, significant heterogeneity (resolvable by RP-HPLC analysis of the reduced monomer) is found when the gene encoding the "native" N-terminal sequence (for example, of the short form, mutein SCSF/C∇150) is expressed. This heterogeneity is eliminated when the corresponding CSF-1 gene lacking the two glutamic acid N-terminal codons is expressed. Correspondingly, N-terminal truncated forms of other short and long CSF-1 gene constructs can also be employed.

For convenience, the primary structure of monomeric proteins encoded by the various cDNA constructs described will be designated herein using a shorthand notation, as follows: LCSF denotes the 522-amino acid sequence disclosed for the clone pcCSF-4, set forth in the Ladner et al article referred to above, *The EMBO J* (1987) 6(9):2693–2698, and shown in FIG. 6. SCSF denotes the 224-amino acid sequence disclosed for the clone pcCSF-17, shown in FIG. 5, described in the Kawasaki article referred to above, *Science* (1985) 230:292–296, also incorporated herein by reference. It will be noted that this particular pcCSF-17 clone has a tyrosine residue at position 59, whereas the gene as defined by the genomic clone has been found to encode aspartic acid at that position. Therefore, $asp_{59}$SCSF denotes a mutein of the disclosed short form having this modification. (The disclosed LCSF clone encodes Asp at position 59.) Muteins corresponding to amino acid substitutions within the "native" sequences depicted are correspondingly designated by the substitution subscripted with the position. Mutein forms of CSF-1 are disclosed in European Patent Application No. 87309409.8, filed 23 Oct. 1987, which is incorporated herein by reference. When constructs putatively encoding these proteins are expressed as mature proteins in bacteria, they may also retain an N-terminal methionine. Since the presence or absence of the N-terminal methionine cannot be predicted, this possibility is not included in the notation.

C-terminal and N-terminal truncations of these basic SCSF and LCSF sequences will be designated as C∇ or N∇, respectively. The C-terminal deletions will be followed by the number representing the number of amino acids of the native structure remaining; for the N-terminal deletions, N∇ will be followed by the number of amino acids deleted from the N terminus. Thus, for example, LCSF/C∇150 denotes a construct encoding a protein which contains the first 150 amino acids of the long CSF sequence; SCSF/C∇158 denotes a construct encoding a protein which contains the first 158 amino acid residues of the short form; SCSF/N∇2 denotes a construct encoding the short form with two N-terminal amino acids deleted. (As set forth above, the LCSF and SCSF diverge beginning at position 150 and reconverge near the C-termini.) LCSF/N∇2C∇150 denotes a form which is the same as LCSF/C∇150, except that the two N-terminal glutamic acid residues are deleted.

Preferred constructions which result in CSF-1 proteins subjected to the process of the invention, include genes encoding LCSF/C∇150, LCSF/C∇190, LCSF/C∇221, LCSF/C∇223, LCSF, and their corresponding N∇2, N∇3, $tyr_{59}$, $ser_{157}$, $ser_{159}$, and $ser_{157}ser_{159}$ forms. Also preferred are SCSF/C∇158, SCSF/C∇150, SCSF, and their corresponding N∇2 and N∇3 and $asp_{59}$ forms.

Particularly preferred starting materials include the products of the genes encoding SCSF/N∇3C∇150, LCSF/N∇3C∇221, $ser_{157}$LCSF/N∇3C∇221, $ser_{159}$LCSF/N∇3C∇221, and $ser_{157}ser_{159}$LCSF/N∇3C∇221.

The resulting proteins may or may not retain the length prescribed by the gene, due to processing by various host systems used for expression. Therefore, although the starting material proteins for refolding are referred to by the same designation, it should be understood that these designations, in reality, refer to the gene construct, and the actual length of the starting material for the process disclosed herein may be shorter or longer (if it has N-terminal Met) than that specified by the C-terminal amino acid number.

C. General Procedure

The starting material for the procedure of the invention is CSF-1 protein produced from the CSF-1-encoding DNA transformed into a bacterial host. The CSF-1 gene can be expressed as a mature protein by utilizing the appropriate CSF-1-encoding DNA which is immediately preceded by an ATG Met-encoding codon or as a fusion protein wherein the CSF-1 sequence is placed in reading frame with a protein-encoding sequence, or in a secreted form by utilizing a signal sequence which is functional in the selected host. If the construct encodes the "mature" form of the protein, the N-terminal methionine may be processed entirely, not at all, or partially. Methionine is, of course, not present at the N-terminus of secreted forms expressed from genes having operably linked signal sequences. Signal sequences are generally those derived from bacterial systems such as penicillinase or phosphatase A. If the secreted form is employed, whether or not secretion is successful, generally the protein is produced in a form more soluble than that obtained when produced as a mature or fusion protein. This generalization is not without exceptions.

If the secreted protein is already soluble, the chaotropic environment may be needed, nonetheless, to effect the refolding procedure. If the protein is formed in insoluble form, initial solubilization is required.

In general, therefore, the process begins with the solubilized monomer in a chaotropic environment, which is maintained under reducing conditions. Such maintenance may involve the use of a suitable reducing agent such as β-mercaptoethanol or dithiothreitol (DTT) but the CSF-1 may already be reduced, and exclusion of oxidizing agents may be sufficient. The solubilized protein is typically maintained in, for example, 8M urea or 7M guanidinium hydrochloride, at a pH of about 7–8.6, in the presence of about 2–100 mM thiol compound. Starting with this solubilized form, the monomer may either be refolded directly or partially purified from remaining proteins by a suitable purification procedure such as chromatography on an adsorbant gel, chromatography using an ion exchange column, or gel-permeation chromatography prior to refolding. Use of a purification step prior to refolding has the advantage of removing contaminating host proteins and materials that may degrade or alter CSF-1. Gel-permeation chromatography is useful, as it permits an easy size separation of the desired monomer length, which is generally known in advance, from impurities of differing molecular weights. As the volume of materials increase, the capacity of gel-permeation columns becomes limiting. For larger volumes, ion exchange chromatography, for example, DEAE chromatography, is preferable. It is required that the purification be conducted under reducing conditions in order to prevent the formation of disulfide-linked aggregates. Thus, regardless of the chromatographic procedure used, a suitable reducing agent is preferably included in the solutions used to load the chromatographic columns or batches and in the eluting solutions. In some instances, low pH, such as pH 6, may be substituted for the reducing agent, as low pH will essentially prevent disulfide bond formation in some chromatographic systems, even in the absence of reducing agent.

The partially purified monomer is then subjected to refolding conditions for the formation of the dimer. The protein concentration during this step is of considerable importance. Final percent yields of dimer per volume of refolding reaction are increased if the protein concentration is less than about 2 mg/ml of the CSF-1 protein; a concentration range of 0.03–0.5 mg/ml is preferred. The use of protein concentrations which are too high may result in formation of undesirable higher-order oligomers. The refolding conditions may include gradual removal of the chaotropic environment over an appropriate time period (usually several hours) or dilution of the sample to the desired concentration of protein and chaotropic agent. Also possible are methods which provide a constant protein concentration, such as dialysis or hollow fiber diafiltration while the chaotrope is slowly removed. At the end of the process, when the chaotropic environment is depleted, a nondenaturing level is reached. For example, if guanidine hydrochloride is used as chaotropic agent, a final concentration of less than about 2M, and preferably 0.1–1M is attained and if urea is used as the chaotropic agent, a final concentration at less than about 1M, and preferably 0.1–0.5M, is attained.

The refolding during removal of chaotropic environment is conducted in a manner so as to permit oxidation of the sulfhydryl groups to disulfides in order to establish the resultant biologically active dimeric configuration which, in the case of CSF-1 is stabilized by the formation of disulfides, one or more of which may link the two chains. Intrachain disulfides are also formed. Suitable redox conditions which encourage this formation of dimer include the sulfhydryl/disulfide reagent combinations, such as oxidized and reduced glutathione. The ratio of reduced to oxidized glutathione or other sulfhydryl/disulfide combination is typically from about 2 mM/0.1 mM to 0.5 mM/1.0 mM. Alternative methods for providing this oxidation are also acceptable. For example, simple removal or dilution of the reducing agent without precautions to exclude air and metal ions effect formation of desirable disulfide linkages. In any event, the pH of the solution during the refolding process should be maintained at about pH 7.5–9.0. It is clear that in the process of refolding, the highly reducing conditions under which the initial purification was conducted are no longer employed. Minimizing the concentration of salts, such as sodium chloride, during the refolding process, permits the use of ion exchange chromatography as a subsequent concentration and/or purification step.

During the refolding process, several dimeric and higher oligomeric species of CSF-1 may be formed including those which have lowered solubility in high salt and higher order oligomers which can be resolved by size exclusion chromatography. This aggregation process is minimized through temperature control, wherein low temperatures of about 0°–4° C. are preferable to higher temperatures of 25°–37° C.

Less stable dimeric forms of CSF-1 which can be resolved as an early eluting peak on reverse-phase HPLC under certain conditions may also form during the refolding process. These less stable forms may result from the formation of undesirable disulfide bonds. Cysteine residues at positions 157 and 159, present in long form CSF-1, are not required for biological activity DNA constructs encoding CSF-1 containing serine substitutions for one or both of these cysteines produce higher yields in the present purification process and may also change solubility characteristics in a desirable fashion.

Residual redox reagents if present in refolded CSF-1 may generate problems during subsequent purification steps. There are many ways to block or prevent the disulfide exchanges which might occur in the presence of such residual redox reagents (e.g., glutathione) including removal by, for example, diafiltration or dialysis; dilution; and lowering the pH of the solution appropriately. Of the above procedures, two of the more preferred procedures are lowering the pH to below pH 7.0 and diafiltration.

After refolding, concentration and/or the initial purification steps are completed, the dimer is further purified from residual redox material and from other proteins using procedures similar to those set forth above for the monomer. It is, of course, not necessary to choose the same purification procedure; indeed it may be preferred to use a different approach than that employed for solubilized monomer purification. Suitable means, in particular, include gel filtration, hydrophobic interaction chromatography, ion exchange chromatography, and reverse-phase HPLC.

For example, prior to further purification of the refolded, dimeric CSF-1, removal of the redox material, if present, and concentration of the refolded proteins may be performed by direct loading of the refolded material onto an ion-exchange chromatography column using, for example, DEAE Sepharose. Frequently, such procedures are carried out at pH's around 8, however, lowering the pH into the range of 5.5 to 7.0 was found to reduce oligomer formation and increase yield of dimeric CSF-1.

The purification of the dimer is required to remove impurities, in particular, pyrogens or other endotoxins which result from the bacterial production of the protein. A particularly successful protocol for removal of these undesirable impurities uses chromatography on a phenyl-TSK or phenyl-Sepharose column. The chromatography is carried out under conditions and with reagents which are endotoxin-free. The desired dimeric CSF-1 is soluble and stable in approximately 1.5M ammonium sulfate at neutral pH, and is loaded onto the columns under these conditions at low temperatures, of about 2° C.–10° C., and preferably about 4° C. In addition, aggregates and unstable forms of refolded CSF-1 are apparently removed from stable dimeric forms of refolded CSF-1 by removal of a precipitate that forms upon the addition of ammonium sulfate. The desired dimeric protein may be eluted using a gradient of decreasing ammonium sulfate with increasing ethylene glycol in neutral buffer. The CSF-1 dimer elutes at approximately 0.6M ammonium sulfate, 35% ethylene glycol from the phenyl-TSK column. Alternative supports can also be used, and phenyl-Sepharose, may be preferred for larger scale production of the purified CSF-1 dimeric protein.

The resulting dimer is of clinical purity. The specific activity of such preparations is approximately equivalent to that of native human CSF-1 produced by mammalian cells. In situations where the starting CSF-1 is of lower purity, or where higher degrees of final purity are required, an additional purification step (such as DEAE chromatography following refolding) may be employed.

In those embodiments which include the additional preliminary step of solubilizing the monomeric form of the protein, the starting materials are obtained as insoluble intracellular protein, which can be separated from soluble bacterial proteins by lysis of the cells under suitable conditions and recovery of the insoluble protein by centrifugation. The recovered insoluble protein is then placed directly into a chaotropic environment to disassemble aggregates and effect solubilization/denaturation.

The recovered, purified dimeric forms are shown to be biologically active using any of several proliferation assays. A standard assay which meets the required criteria is the in vitro colony-stimulating assay of Metcalf, D., *J Cell Physiol* (1970) 76:89. The presence of CSF-1 in this system results in the formation of predominantly macrophage colonies. Another assay is increase in cell proliferation, as measured by $^3$H thymidine incorporation in a CSF-1-dependent cell line such as the mouse macrophage line BAC. In another form of this assay, a colorimetric detection system based on the reduction of the tetrazolium salt, MTT, can be used. The CSF-1 dimers resulting from the process of the invention are active in such assays and are essentially free of other proteins produced by the bacteria.

Importantly, the CSF-1 preparations are clinically pure. They are substantially free of endotoxin, having less than about 1.0 ng endotoxin/mg of CSF-1 as assayed by the standard limulus amebocyte lysate (LAL) assay, Associates of Cape Cod, Inc., Woods Hole, Mass. Further purification may be desired, but preparations of approximately 95% or more purity in CSF-1 protein, as determined by SDS-PAGE, are obtained by the method of the invention. Further, the specific activity is approximately equivalent to or higher than that of the native protein.

D. Pharmaceutical Compositions

The refolded and clinically pure CSF-1 preparations can then be formulated for administration by conventional protocols and regimens, preferably systemic, including intravenous administration. The compositions may include conventional excipients, such as water for injection, buffers, solubilizing agents, and stabilizers, as is known in the art. A summary of formulation techniques for pharmaceutical compositions, including protein, is found, for example, in *Reminqton's Pharmaceutical Sciences*, Mack Publishing Co., Easton, Pa., latest edition.

E. Heterodimer Formation

It should be noted that the process of the invention permits the formation of heterodimers from among various monomeric units of CSF-1. For example, the large number of CSF-1 proteins formed by variations in C-terminal processing provides a variety of starting materials which can be utilized in dimer formation. Thus, novel heterodimeric materials can readily be formed. For example, the monomeric form of SCSF/C∇150, along with the monomeric form of LCSF/C∇190, can be mixed and treated according to the method of the invention; the heterodimer can then be separated from the homodimer side products by various chromatographic methods. Similar mixtures subjected to the method of the invention lead to heterodimers of components having amino acid substitutions —e.g., $glu_{52}$ LCSF and LCSF/C∇190.

The differing monomers may be mixed in vitro or produced in the same cell. If produced in the same cell, a construct for expression of each monomer is introduced into the same host; in such embodiments, it is preferred that each construct bear a different marker (such as $Tc^R$ and $Amp^R$) so that cotransformed hosts are selected. The cotransformed cells are then grown and induced to obtain mixtures of the two forms.

EXAMPLES

The following examples are intended to illustrate, but not to limit, the invention.

EXAMPLE 1

This example describes the recovery of purified, biologically active protein expressed from a construct encoding $asp_{59}$SCSF/C∇150 in *E. coli* under control of the $P_L$ promoter in a vector constructed as described in European Patent Application No. 87309409.8, filed 23 Oct. 1987, published June 29, 1988 as European Patent Publication No. 0272779 assigned to the same assignee and incorporated herein by reference. The protein is produced in a monomeric, insoluble form intracellularly.

An *E. coli* λ lysogen, DG116, transformed with the plasmid over-expresser (O/E) $pP_L$SCSFasp59/C∇150, CMCC cell line deposit no. 2948, were grown in a 10 l fermenter in basal medium containing 72 mM $(NH_4)_2SO_4$, 20 mM $KH_2PO_4$, 2.0 ml/l TK9, with sterile additions of 10 g/l glucose, 3.0 mM $MgSO_4°7H_2O$, 72 μM $FeSO_4$, 20 mg/l thiamine°HCl, and 50 mg/l ampicillin.

The cells were grown at 30° C. to $OD_{680nm}$ of 12; casamino acids were added to 2%; and then CSF-1 expression was induced by shifting to 42° C. The cells were then grown for 3 more hours to a final $OD_{680nm}$ of 16.5.

The cells were harvested by centrifugation and homogenized using 30 min sonication at 4° C. The homogenate was then centrifuged and the cell debris retained. The debris contained the insoluble protein, which was resuspended in 30% sucrose and centrifuged at 15,000 × g for 10 min at 4° C. to enrich for the insoluble protein.

The pellet from the centrifugation was solubilized in 7M guanidine HCl in 0.1M sodium phosphate, pH 7, containing 50 mM DTT and 5 mM EDTA for 30 min. The suspension was then heated to 40° C. for 5 min and the supernatant recovered after centrifugation. The recovered supernatant was loaded onto a 90×2.6 cm Sephacryl (S-200) column equilibrated in the same buffer, but containing 2 mM DTT rather than 50 mM. The column was run using the same buffer, and the protein concentration was monitored by 280 nm adsorption with the results shown in FIG. 1. The majority of the bacterial proteins were separated from CSF-1, which was recovered as a 17 kd peak representing approximately 80% pure CSF-1 monomer.

Figure 2A:
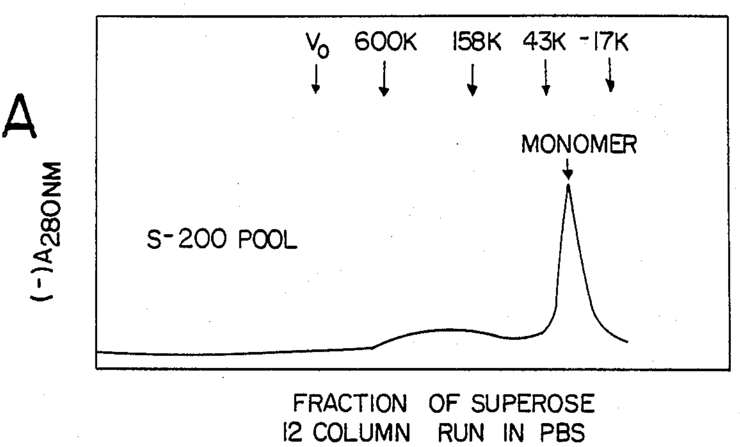
FIGS. 2A, 2B and 2C show the extent of dimerization as assayed using molecular sieve chromatography.
Figure 2B:
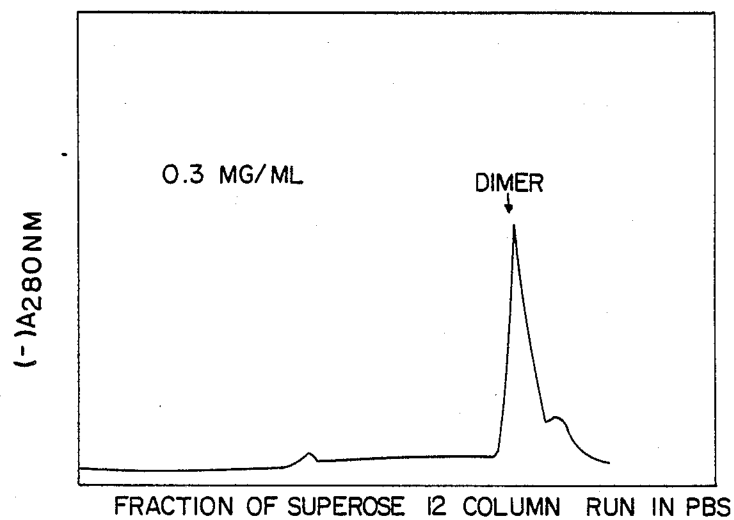
Figure 2C:
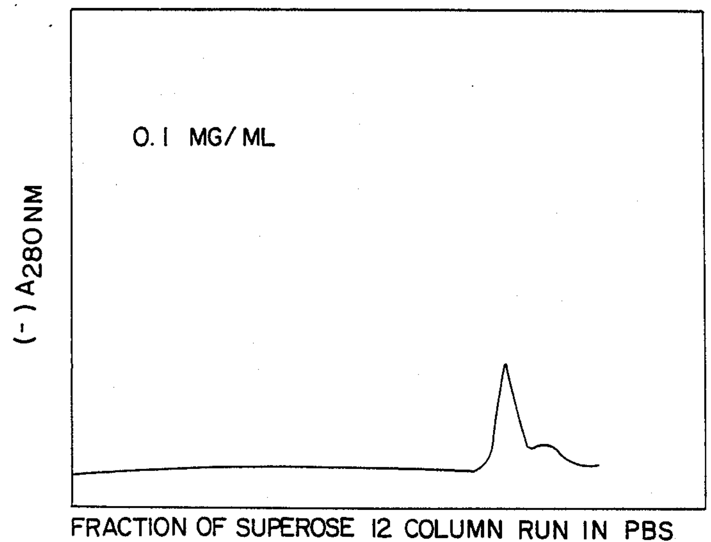

The CSF-1 pool was then diluted to 0.25 mg/ml protein in a corresponding buffer containing 7M guanidine hydrochloride, 50 mM Tris, pH 8.5, and 5 mM EDTA which contained a redox system, consisting of 2 mM reduced glutathione (GSH) and 1 mM oxidized glutathione (GSSG). To refold the partially purified CSF-1, the pool from the S-200 column was dialyzed against this buffer (containing 7M guanidine hydrochloride and GSH/GSSG), and then allowed to fold by slowly adding a solution of 50 mM Tris, pH 8.5, 5 mM EDTA, and the GSH/GSSG in 0.1M NaCl to the dialysis vessel. The addition was carried out at 4° C. over 48 hr until the final guanidine concentration was approximately 0.2M. The dialyzate at this point contained dimeric CSF-1, which was loaded directly onto a Superose 12 molecular sizing column equilibrated in phosphate-buffered saline for further purification. Elution was again followed by 280 nm absorption. The elution pattern is shown in FIG. 2. Before exposure to refolding conditions, the CSF-1 eluted as would be expected for the monomer (FIG. 2*a*); however, when the protein was exposed to refolding conditions at 0.3 mg/ml, as described above (or, alternatively, at 0.1 mg/ml), results show the formation of the dimer-sized material, as indicated in FIGS. 2*b* and 2*c*, respectively.

Figure 3A:
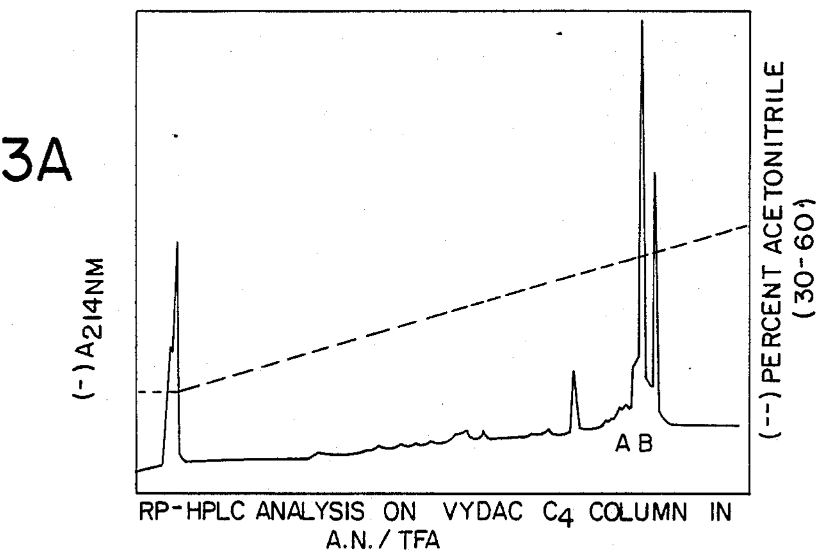
FIGS. 3A, 3B and 3C represent RP-HPCL analysis of one type of denatured and refolded recombinant *E. Coli* CSF-1.
Figure 3B:
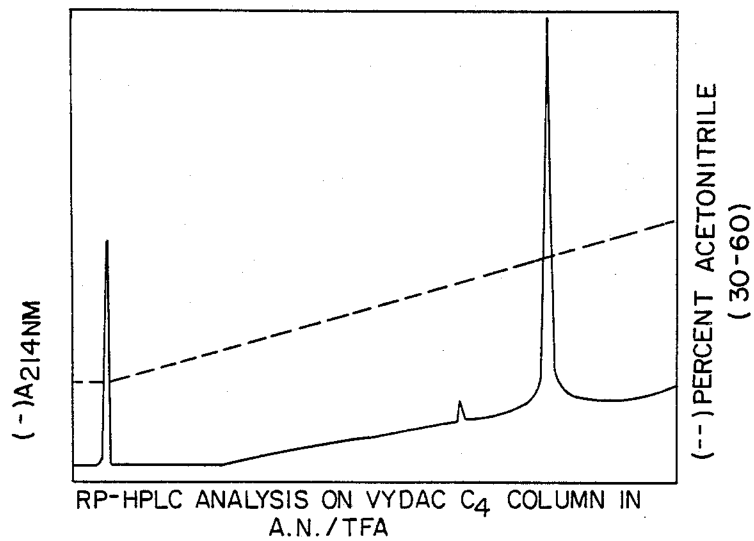
Figure 3C:
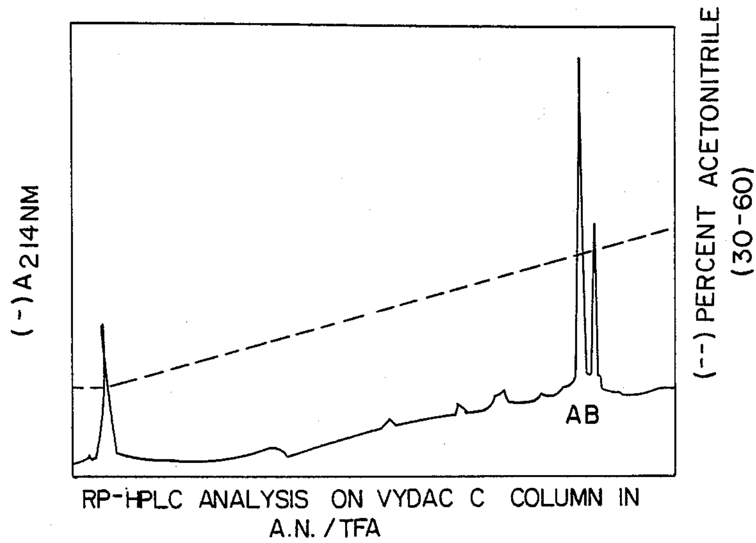
Figure 7:
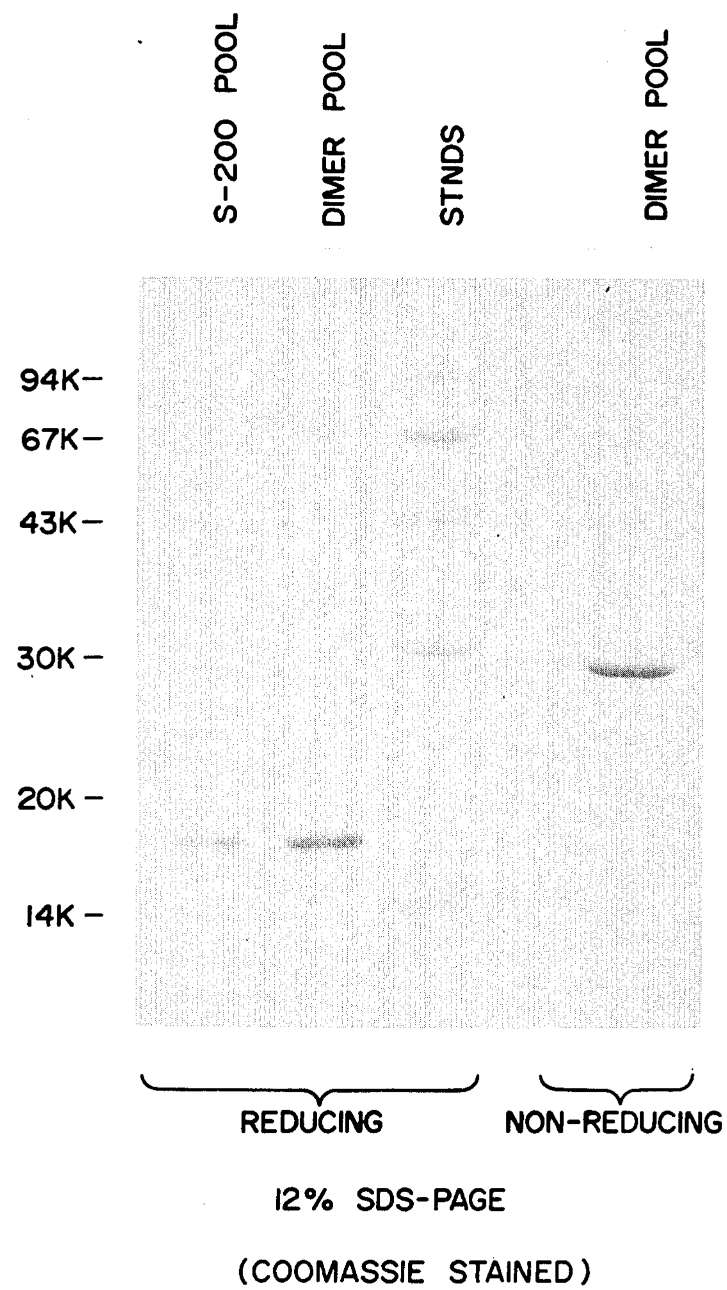
FIG. 7 shows the results of a reducing and non-reducing SDS-PAGE analysis of dimeric $asp_{59}$SCSF/C∇150 CSF-1.

The dimeric product chromatographed as a single peak on reverse-phase HPLC, as shown in FIG. 3*b*. The dimeric product is over 90% a single species on RP-HPLC (see FIG. 3*b*) and shows satisfactory stability and full biological activity. With respect to other proteins the CSF-1 is shown to be over 95% pure by reducing and non-reducing SDS-PAGE analysis (FIG. 7). Results for the S-200 pool starting material before refolding, shown in FIG. 3*a*, indicate a predominance of monomer (which elutes as two major peaks of CSF-1). However, the single dimer peak illustrated in FIG. 3*b* was shown to consist of two major components following re-reduction to the monomer (FIG. 3*c*) as separated by RP-HPLC.

Figure 4A:
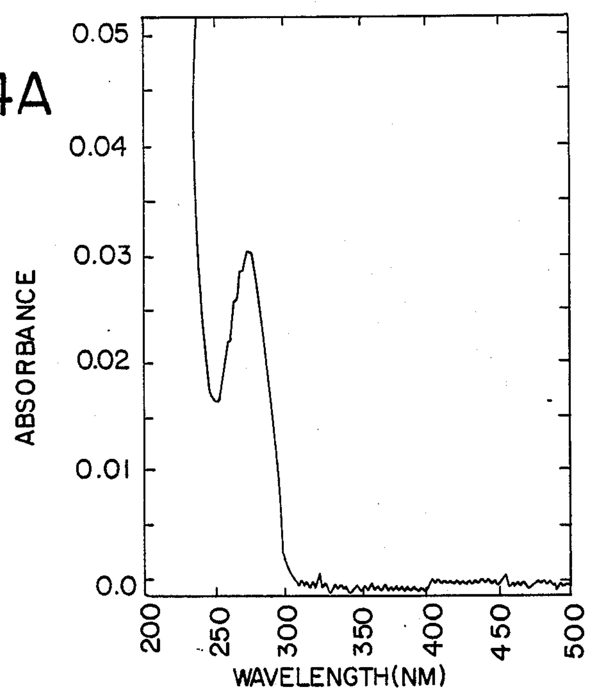
FIGS. 4A and 4B show a spectral analysis to determine the solubility of one type of denatured and refolded recombinant *E. coli* CSF-1.
Figure 4B:
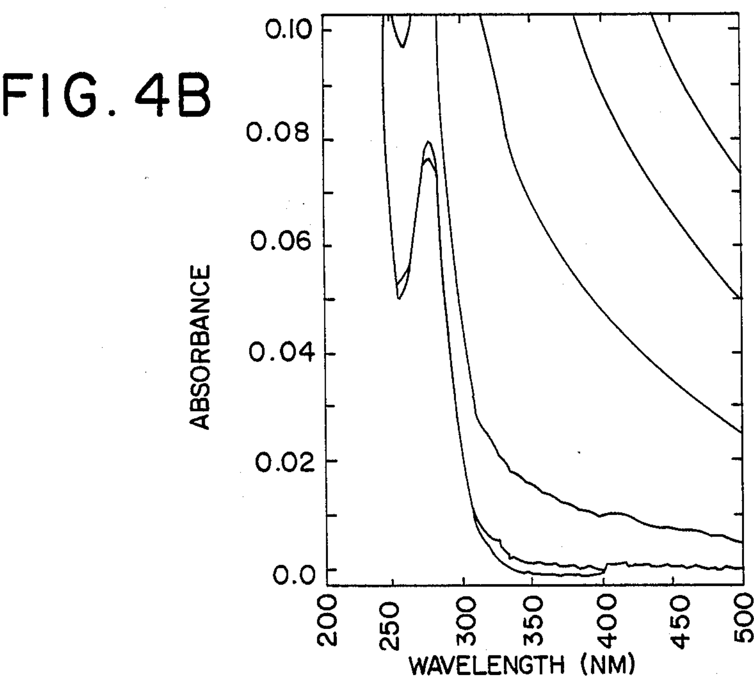

The protein product was characterized for solubility by UV-visible spectroscopy. Spectra were recorded at 30-min intervals following dilution of the purified dimeric pool in phosphate-buffered saline, as shown in FIG. 4. As shown in panel A, over a 2-hr period the spectrum of the final product remained constant, indicating that the refolded protein was stable and soluble under physiological conditions. In contrast, a similar spectral analysis on the monomeric starting material, shown as panel B in FIG. 4, at 90-sec intervals showed that the protein was unstable and rapidly formed insoluble, light-scattering aggregates.

The purified dimeric material prepared above was assayed in the mouse bone-marrow colony assay in duplicate, along with a "control" consisting of purified recombinant CSF obtained from a gene of similar sequence (SCSF) expressed as an active secreted molecule of approximately 158 amino acids in the mammalian cell line CV-1. The refolded *E. coli* CSF-1 has a mouse bone marrow assay specific activity (in U/mg) of $2\text{–}4\times10^7$, as compared to about $3\times10^7$ U/mg for CSF-1 obtained from CV-1 cells. The purified unrefolded starting material had a specific activity approximately 1000-fold lower. (The mouse bone marrow assay was by Moore, R., et al, *J Immunol* (1983) 131:2374–2378 and by Prystowsky, M., et al, *Am J Pathol* (1984) 114:149. Human CSF-1 shows about 10-fold greater activity in a murine bone marrow assay as compared to activity in a human bone marrow assay.)

Native CSF-1, purified from MIAPaCa cells had a mouse bone marrow assay specific activity of $4\text{–}8\times10^7$ U/mg.

The circular dichroism (CD) spectrum of the refolded *E. coli* protein was essentially identical within experimental error to that of "naturally folded" CSF-1 from CV-1 cells.

EXAMPLE 2

Twenty grams of frozen *E. coli* DG116 paste from cells expressing a construct encoding $asp_{59}$SCSF/C∇150 under control of the $P_L$ promoter were resuspended in 200 ml of 50 mM Tris, 10 mM EDTA (pH 8.5) and sonicated for 30 min in an ice bath, 60% pulse, intensity of 9.

The cell debris was retained following 10 min ×15,000×g centrifugation. The cell debris was resuspended in 200 ml of 30% sucrose (in 10 mM EDTA, pH 8.0) and sonicated 3 min to break up clumps and free insoluble protein. The suspension was then centrifuged for 15 min×15,000×g, and the pellet was retained.

The sucrose-purified insoluble protein was then solubilized in 15 ml of 0.45 μ filtered 7M guanidine HCl (GuHCl), 0.1M sodium phosphate, 5 mM EDTA, 50 mM DTT (pH 7.5–8.0) for approximately 15 min and then heated to approximately 37°–40° C. for 10 min to insure reduction of disulfide bonds. The solubilized material was then centrifuged for 10 min×15,000×g.

Six to ten ml of the clarified, solubilized CSF-1 was loaded onto a 2.6 ×95 cm S-200 column equilibrated in filter-sterilized S-200 buffer (7M GuHCl, 0.1M sodium phosphate, 5 mM EDTA, 2 mM DTT, pH 6.8) and sized overnight at room temperature at 1 ml/min. The protein eluted as a well-resolved peak, and when pooled, contained 40–70 mg of protein at about 1.2–1.5 mg/ml (40–60 ml).

The protein content was determined by absorbance at 280 nm, assuming that 1 $A_{280}$ equals 1 mg/ml. The solution was then diluted to 0.1–0.15 mg/ml protein, 0.5–0.7M GuHCl, in buffer-containing 50 mM Tris (pH 8.5), 100 mM NaCl, 5 mM EDTA, 2 mM reduced glutathione (GSH), 1 mM oxidized glutathione (GSSG), by addition of the appropriate buffer to the protein solution and letting it sit 24 hr at 4° C.

Solid ammonium sulfate was added to 1.2M final concentration and the pH was then adjusted to 7.0. At this point a precipitate formed which contained incorrectly folded forms of CSF-1. This can be at least partially recovered and recycled (see below). The CSF-1 preparation was then prepared for further removal of pyrogens/endotoxins and residual contaminants on a phenyl-TSK column. All buffers and reagents are prepared pyrogen-free. The CSF-1 preparation was centrifuged 10 min×15,000×g and filtered through a 0.45 μ filter (500 ml) disposable unit before being pumped onto a phenyl-TSK HPLC column equilibrated in 1.5M ammonium sulfate, 0.1M sodium phosphate (pH 7.0) run at 4° C.

After loading the CSF-1, the column was washed for 30 min. The protein was then eluted with a 45-min gradient of decreasing ammonium sulfate, increasing ethylene glycol B buffer (B buffer=60% ethylene glycol, 0.01M sodium phosphate (pH 7.0)). The CSF-1 protein eluted at approximately 0.6M ammonium sulfate, 35% ethylene glycol.

The first major peak that eluted was biologically active, dimeric CSF-1. The CSF-1 peak was pooled and then extensively dialyzed against 5% mannitol, 25 mM sodium phosphate (pH 7.4), filter sterilized, and stored at 4° C. Endotoxin content varied from 0.1–1 ng/mg.

In a similar manner, *E. coli* protein produced under control of the $P_L$ promoter from DNA encoding $asp_{59}$SCSF/N∇2C∇150, $asp_{59}$SCSF/N∇3C∇150, N∇3C∇158, LCSF/C∇190, and LCSF/C∇221 was refolded and purified. The final preparations contained 6–15 mg of purified CSF-1 with an approximate overall yield of 15–30%, and a specific activity of 5–10 $\times10^7$ U/mg in the mouse bone marrow assay (using $A_{280}$ and assuming a value of 1.0 corresponds to 1 mg CSF-1 per ml). The preparations also have approximately the same specific activity in human bone marrow assay as purified native MIAPaCa CSF-1.

EXAMPLE 3

Direct Refolding of Solubilized Refractile Bodies

Sucrose-purified, solubilized $asp_{59}$SCSF/C∇150 refractile bodies were prepared as in Example 2, and had a protein concentration of 20 mg/ml. For refolding, the protein concentration was decreased by diluting to 1.5 mg/ml $asp_{59}$SCSF/C∇150 (total CSF-1 was 38 mg) in 7M GuHCl, 0.1M sodium phosphate (pH 7.0), 5 mM EDTA, 1 mM DTT. Refolding was initiated by diluting tenfold to 0.15 mg/ml in 50 mM Tris (pH 8.5), 100 mM NaCl, 5 mM EDTA, 2 mM GSH, and 1 mM GSSG (same refolding buffer as above) at 4° C. and allowed to proceed 24 hr.

Approximately 35% of the CSF-1 monomer refolded into dimeric form (based on the known retention time of dimeric CSF-1) as detected by RP-HPLC. The purity of the refolded dimers was estimated to be about 63% by RP-HPLC.

EXAMPLE 4

Recycling Aggregates

The precipitate described in Example 2 presumably contains incorrectly folded forms of CSF-1. When formed from refolding of about 38 mg of protein, it constituted about 10 mg of pelletable precipitate. This precipitate was dissolved in the S-200 buffer containing 7M GuHCl and 2 mM DTT (described in Example 2). The suspension was heated at 37° C. for 15 min to reduce any disulfide bonds, and the resulting clear solution was cooled to 4° C. The solution was then diluted to 0.7M GuHCl in refolding buffer and allowed to refold, as described above. Ammonium sulfate was then added and the CSF-1 refolded dimer was purified from the resulting solution to remove pyrogens/endotoxins by phenyl-TSK HPLC as described above. This yielded over 3 mg of soluble, dimeric CSF-1.

This recycling process, when carried out at larger scale, is expected to significantly improve the overall yield of the process for producing refolded CSF-1.

EXAMPLE 5

*E. coli* strain DG116 was transformed with plasmid vector pLCSF221A, a plasmid containing the gene encoding asp$_{59}$LCSF/N∇3C∇221. The transformed *E. coli* strain DG116 was deposited with the American Type Culture Collection under accession no. ATCC 67390, on 14 April 1987. The transformed host was grown in a 100 l standard air-sparged Rushton turbine fermenter in basal medium containing 96 mM $(NH_4)_2SO_4$, 28 mM $KH_2PO_4$, 4 mM $Na_3$ citrate°2 $H_2O$, 1.7 ml/l TK9 (30 mM $ZnSO_4$, 30 mM $MgSO_4$, 1 mM $CuSO_4$), with sterile additions of 6.5 g/l glucose, 2.2 mM $MgSO_4$°7 $H_2O$, 95 μm $FeSO_4$°7 $H_2O$ and 26 mg/l thiamine°HCl at 30° C. until an $OD_{680nm}$ of 10 was reached. The culture was then induced by temperature shift to 37° C. with concurrent sterile additions of casamino acids to 2.3% (w/v) final concentration and $MgSO_4$°7 $H_2O$ to 1.7 mM final concentration.

Four hours post-induction, the cells were harvested by five-fold concentration and diafiltered against 10 volumes of 5 mM EDTA, pH 8.5, using DorrOliver tangential cross-flow microporous filtration. The cells were disrupted by three passes at 7,500 psi in a Manton-Gaulin high pressure mechanical cell homogenizer. 1-Octanol was added to 0.1% (v/v) and the homogenate held overnight at 4° C.

The homogenate was made 25% sucrose by addition of a 63% w/v sucrose solution. The insoluble protein fraction (refractile bodies) was separated from cell debris by continuous flow disk stack centrifugation (Westphalia SB7) at 9000 ×g, 1 liter/minute and 4°-6° C. The wet pellet was mixed 50:50 (w/v) in deionized water and stored at −20° C. in 45 g aliquots.

Ninety grams refractile body suspension was thawed at room temperature and homogenized in 200 ml 0.1 M Tris, pH 8.5, containing 25 mM EDTA and 10 mM DTT using a Tekmar tissumizer for 1 minute at 50% speed. The suspension was adjusted to 1 liter 8M urea, 2 mM DTT, 5 mM EDTA and 20 mM Tris, pH 8.5 and stirred for approximately 30 minutes at room temperature. Insoluble debris was removed using a 1 sq. ft. 0.8–0.2 μm Sartorius disposable membrane filter cartridge.

Following filtration, the suspension containing reduced CSF-1 monomer was partially purified by DEAE chromatography. Sample at an $A_{280}$ of 10 (500 ml) was applied to each of two 5×45 cm DEAE Sepharose fast flow columns equilibrated in 0.1M Tris, pH 8.5. Each column was developed using a 3600 ml, 0–0.4M NaCl gradient in 4M urea, 0.1M Tris, pH 8.5, 5 mM EDTA, and 2 mM DTT. Based on the assumption that 1 $A_{280}$ equals 1 mg/ml, 4.5 g of protein were recovered.

DEAE purified CSF-1 monomer was cooled to 4° C. and diluted 1:10 in pre-chilled 50 mM Tris, pH 8.5, containing 5 mM EDTA, 2 mM reduced glutathione, and 1 mM oxidized glutathione to a final estimated protein $A_{280}$ absorbance of 0.2. Although initial dimer formation was essentially complete within 24 hours as judged by SDS-PAGE, the refolding mixture (22.5 liters) was held for five days at 4° C. to maximize yield of CSF-1 dimer with the correct conformation. The conformation of dimeric CSF-1 in the refolding mixture was assessed by reverse-phase HPLC. Using a $C_4$ column and a 35–55% acetonitrile gradient, dimeric CSF-1 eluted as two discrete species; stable active CSF-1 was the more hydrophobic. This stable, active CSF-1 species represented 65% of the protein after five days incubation.

Reduced and oxidized glutathione were removed by diafiltration against 20 mM sodium phosphate, pH 7, and the protein concentrated to an $A_{280}$ absorbance of 1.2 using an Amicon 10 sq. ft. PM10 hollow fiber cartridge. Ammonium sulfate was added to the diafiltered material to a concentration of 1.2M. Precipitated unstable conformer (the less hydrophobic species detected by reverse-phase HPLC) was removed by filtration. The filtrate (2 g stable dimeric CSF-1) was applied to a 5×20 cm bed of fast flow phenyl Sepharose equilibrated in 1.2M ammonium sulfate containing 0.0025M sodium phosphate, pH 7.0, and eluted in 6 hours in a simultaneously decreasing (0.72M to 0M ammonium sulfate) and increasing (24% to 60% v/v ethylene glycol) gradient of 1500 ml in 0.01M sodium phosphate buffer, pH 7.0. Dimeric CSF-1 eluted at approximately 30–35% ethylene glycol and was well separated from tetrameric CSF-1 and endotoxin, both of which eluted later. Dimeric CSF-1 was diafiltered against 20 mM sodium phosphate, pH 7.5, and concentrated to an $A_{280}$ of 10 using a 1 sq. ft. Amicon spiral cartridge (YM10). The recovery was 1.3 g stable dimeric CSF-1 based on $A_{280}$. CSF-1 produced had a biological activity of about $6\times10^7$ U/mg using a CSF-1-dependent cell proliferation assay to determine activity. The final product was 98.6% dimer and 93% reducible dimer, determined by nonreducing and reducing SDS-PAGE analysis. The endotoxin content was 0.01 ng/mg of CSF-1 as determined by LAL assay and $A_{280}$ nm.

EXAMPLE 6

DEAE Chromatocraphy Following Refolding

An *E. coli* strain HW22, transformed with the plasmid pJN653 containing the asp$_{59}$SCSF/N∇3C∇158 gene was grown in a 10-liter fermenter in the same medium described in Example 5. The cells were grown at 30° C. to an absorbance at 680 nm of 10, and casamino acids were then added to 2%. CSF-1 expression was induced by shifting the temperature of the culture to 37° C. After 4 hr the absorbance at 680 nm reached 79; the cells were harvested, homogenized and refractile bodies were prepared as described in Example 5.

Twenty-five grams of refractile body suspension (approximately 390 g of protein) were solubilized in 250 ml of 8M urea containing 25 mM Tris, 10 mM sodium phosphate buffer (pH 8.4), 1 mM EDTA and 4 mM DTT. After 2 hr at room temperature, the solution was clarified by centrifugation at 15,000×g for 15 min. A 150 ml aliquot of the solubilized CSF-1 was then loaded onto a 5×8 cm DEAE-Sepharose (Pharmacia) column equilibrated in 6M urea containing 25 mM Tris and 10 mM sodium phosphate buffer (pH 7.0). The column was washed with 1 bed volume of the above solution which had been modified to contain 1 mM DTT and 1 mM EDTA, and the CSF-1 was then eluted with a 1.4 l salt gradient of 0–0.6M sodium chloride in the wash buffer. The CSF-1 peak eluted at approximately 0.06M sodium chloride. The remaining 90 ml of solubilized refractile bodies were then purified over the DEAE-Sepharose column in identical fashion. The combined CSF-1 pools (165 ml) contained approximately 250 mg of protein at a purity of approximately 50%.

The CSF-1 was then refolded by diluting the DEAE pool 10-fold into refolding buffer containing 50 mM Tris (pH 8.5), 5 mM EDTA, 2 mM reduced glutathione, 1 mM oxidized glutathione, precooled to 4° C. The CSF-1 was allowed to refold for 30 hrs at 4° C. The pH of the refolded CSF-1 was adjusted to 6.8 using 8.5% phosphoric acid solution. The solution was clarified by centrifugation for 10 min at 15,000×g and loaded onto a 5 ×4 cm DEAE-Sepharose column pre-equilibrated in 10 mM sodium phosphate, 25 mM Tris (pH 6.8). The column was washed with 300 ml of this buffer and eluted with a 700 ml 0–0.6M sodium chloride gradient in the same buffer system. The CSF-1 eluted at approximately 120 mM sodium chloride. Ammonium sulfate (4M stock, pH 7.0) was added to the 95 ml DEAE pool to a final concentration of 1M. The CSF-1 was filtered through a Nalgene 0.45 micron filter and loaded (at 4° C.) onto a 21.5×150 mm Bio-Rad TSK Phenyl-5-PW column equilibrated in depyrogenated 1.5M ammonium sulfate and 0.1M sodium phosphate (pH 7.0). The column was washed with two bed volumes of this loading buffer and eluted in 0.1M sodium phosphate (pH 7.0) using a 45-min gradient in which the ammonium sulfate concentration decreased from 1.5M to 0M and the ethylene glycol concentration increased from 0–60%. All operations were carried out at 4° C. under essentially pyrogen-free conditions. The CSF-1 eluted at approximately 0.6M ammonium sulfate in 30% ethylene glycol. The CSF-1 was extensively dialyzed into 10 mM HEPES buffer (pH 7.5) containing 150 mM sodium chloride and filter sterilized through a Millex 0.45 micron filter.

Approximately 50 mg of purified $asp_{59}$SCSF/N∇3 C∇158 CSF-1 was obtained. The final CSF-1 product was greater than 90% single species by SDS-PAGE analysis and approximately 96% pure by RP-HPLC in acetonitrile/TFA. The specific activity was $1.7\times10^8$ $\mu$/mg (units determined as colony forming units equivalents using a CSF-1-dependent cell line, and protein concentration determined using $A_{280nm}$ and an assumed extinction coefficient of 1.0). This specific activity is at least equivalent to, if not greater than, that of native Mia PaCa CSF-1. The endotoxin content, determined by LAL assay was 0.5–1 ng/mg of CSF-1.

EXAMPLE 7

An alternative purification method was used to process a refolding reaction of LCSF/N∇3 C∇221 prepared according to method of Example 5 up to and including the refolding step. In this modified method, the refolded CSF-1 was directly loaded onto an anion exchange column. At pH 6.8, the redox system reagents flowed directly through the anion exchange column, while the CSF-1 remained bound and concentrated on the column. In this manner, the CSF-1 was separated from the redox system at a pH where thio-disulfide exchange reactions were minimized, thus preventing the significant oligomer formation that was found to occur if this step was performed at higher pH (8.5).

Five ml of refolded CSF-1 (1 mg total protein from the refolding reaction described in Example 5) was directly loaded onto a 7.5 × 75 mm Bio-Rad TSK DEAE-5-PW column after lowering the pH of the refolded CSF-1 to 6.8 using a 1M phosphoric acid solution. The DEAE column had been equilibrated in 10 mM sodium phosphate, 25 mM Tris (pH 6.8). After loading the CSF-1, the column was washed with two bed volumes of this buffer and then eluted with a 45 min 0–0.6M sodium chloride gradient in the same buffer. The column separated dimeric CSF-1 from monomeric and oligomeric forms of CSF-1 (as determined by non-reducing SDS-PAGE and Western analysis of the DEAE fractions). The yield of dimeric CSF-1 was approximately 70%. This is a 5-fold greater yield than that obtained when the same purification was performed at pH 8.5. Subsequent to this DEAE-purification step, the CSF-1 would be purified away from contaminating endotoxins and the unstable form of the CSF-1 dimer as described in Example 6, beginning with the ammonium sulfate addition which precedes the phenyl-Sepharose step.

EXAMPLE 8

An alternative method for the refolding of CSF-1 has been utilized. Plasmid pLCSF221A was induced in *E. coli* and the expressed protein processed in substantial accordance with the teaching of Example 5 with some modifications. For example, the harvested cells were diafiltered against 5 mM EDTA with no pH adjustment. After the second pass through the homogenizer, the pH was adjusted to 6 with acetic acid. In addition, air oxidation was relied upon for formation of disulfide bonds during refolding of the CSF-1 molecule.

DEAE-purified CSF-1 monomer was diluted to a final concentration of 0.2 mg/ml in 50 mM Tris pH 8.5, 5 mM EDTA, and refolded for 4 days at 4° C. in the presence or in the absence of the glutathione redox system. The refolded proteins were further purified in substantial accordance with the procedures described in Example 5, again with some modification. The refolded dimeric mixture was diafiltered and concentrated to an OD of 1. After the ammonium sulfate precipitation, the sample was applied to a phenyl-Sepharose fast flow column and then eluted in a decreasing (0.78 to 0.18M ammonium sulfate) gradient of 1800 ml in 0.01M sodium phosphate buffer (pH 7). The dimer elutes at ~0.6M ammonium sulfate. Lastly, the dimeric CSF-1 was diafiltered against 0.588% sodium citrate and 0.645% NaCl at pH 7. In the absence of the glutathione redox system, the diafiltration step required for glutathione removal may be omitted.

Final products from the refoldings done in the presence or in the absence of a redox system were compared by SDS-PAGE, RP/HPLC, isoelectric focusing and bioassay. Similar molecular weights and purities (95% by densitometry scanning) under both reducing and non-reducing conditions of 12% SDS-PAGE visualized by Coomassie staining were observed for both refolded samples. Reverse-phase HPLC analysis was also used to compare the refolding kinetics after 5 or 12 days of CSF-1 refolding in the presence or absence of the glutathione redox system. These samples were immediately run on a $C_4$ Vydac column with a 35–55% acetonitrile, 0.1% TFA gradient elution developed over 30 minutes. Both systems resulted in two major dimeric species having similar retention times and which appeared to be in a relatively stable equilibrium over the time period analyzed. Phast (Pharmacia) isoelectic focusing (IEF) gels of 1.0 $\mu$g each of the refolded CSF-1 preparations showed similar ionic patterns, containing a major ionic species with a pI of approximately 4.7 and a slightly more acidic minor species. Both spontaneously refolded CSF-1 and CSF-1 refolded using the redox system had specific activities of $1.2\times10^8$ U/mg in the NSF-60 cell proliferation assay. Thus the CSF-1 produced by these two refolding systems appeared to be essentially identical in product purity and biological activity, as assayed by the criteria described. Overall yields were also comparable for the two processes.

In addition to deleting the diafiltration step for glutathione removal, the concentration step may be replaced by an alternative purification step in which the large volume of refolded dimer CSF-1 is directly applied to a second anion exchange column for concentration prior to ammonium sulfate precipitation and subsequent purification by hydrophobic interaction chromatography.

EXAMPLE 9

CSF-1 constructs in which certain cysteines have been changed to serines have also been successfully refolded. These refolded proteins are fully active in vitro, but have slightly different RP-HPLC retention times. For example, the double-serine construct, $ser_{157}ser_{159}$LCSF/N∇3C∇221, was refolded using the procedure described in Example 5, and this resulted in a CSF-1 preparation which displays a single peak on RP-HPLC. When either of the single-serine constructs, $ser_{157}$LCSF/N∇3C∇221 or $ser_{159}$LCSF/N∇3C∇221, were refolded, a modified refolding protocol was required in order to obtain a product which was homogeneous when analyzed on RP-HPLC. These two products both eluted with a later retention time than the $ser_{157}ser_{159}$LCSF/N∇3C∇221 refolded product, yet were again fully active in vitro.

*E. coli* strain DG116 was transformed with either the plasmid vector pLCSF221B or pLCSF221C, plasmids containing the gen encoding $ser_{157}$LCSF/N∇3C∇221 or $ser_{159}$LCSF/N∇3C∇221, respectively. These two *E. coli* strains were grown in shake flasks at 30° C. in 500 ml of the same medium desribed in Example 5 (final $A_{680nm}$ of 0.2). CSF-1 expression was induced by shifting the temperature of the culture to 42° C. After 4 hr, the culture was harvested by centrifugation and the cells resuspended in 30 ml of 50 mM Tris buffer (pH 8.5), 5 mM EDTA. The cells were lysed by sonciation and the cell debris retained following centrifugation. Refractile bodies were then isolated by resuspending the cell debris in 30% sucrose and pelleting the refractile bodies by centrifugation. The refractile bodies were solubilized in 10M urea, 10 mM Tris (pH 8.5), 1 mM EDTA, and 5 mM DTT. Insoluble material was removed by centrifugation, followed by filtration through a 0.2 micron Millex filter. The CSF-1 monomers were then purified from the filtrate, using ion exchange chromatography on a Bio-Rad TSK DEAE-5-PW column (7.5×75 mm) equilibrated in 6M urea, 10 mM Tris (pH 8.5) containing 1 mM EDTA and 1 mM DTT. The CSF-1 was eluted with a 45 min, 0–0.4M sodium chloride gradient. CSF-1 eluted early in the gradient as the single, major protein peak. The protein was pooled and the absorbance at 280nm determined. The CSF-1 was refolded by diluting into a solution containing 50 mM Tris (pH 8.5), 5 mM EDTA, 2 mM reduced glutathione, and 1 mM oxidized glutathione to a final $A_{280nm}$ value of 0.2 as calculated from the undiluted DEAE pool $A_{280nm}$ absorbance. The CSF-1 was allowed to refold for 48 hr at 4° C.

At this point an additional oxidation step was added to the refolding protocol in order to obtain a product which was essentially homogeneous by RP-HPLC analysis. The refolded CSF-1 protein was dialyzed at 4° C. for 24 hr in 0.4M urea, 50 mM Tris (pH 8.5), 5 mM EDTA containing only reduced glutathione (2 mM). This step may remove glutathione bound to the protein through a mixed disulfide. 1M phosphoric acid was then used to adjust the pH to 6.5, thereby decreasing the rate of thio-disulfide exchange. The CSF-1 was purified by ion exchange chromatography on a Bio-Rad TSK DEAE-5-PW column equilibrated in 10 mM sodium phosphate, 25 mM Tris buffer (pH 6.5). This step removes residual glutthione and further purifies the protein. The protein was eluted with a 45 min, 0–0.6M sodium chloride gradient. The refolded, CSF-1 dimer pool was then subjected to cupric chloride oxidation using a modification of the method taught in U.S. Pat. No. 4,572,798, which patent is incorporated herein by reference. The CSF-1 was diluted to 0.2 absorbance units ($A_{280nm}$) in 10 mM sodium phosphate, 25 mM Tris buffer (pH 6.5) and treated with 50 micromolar cupric chloride for 2 hr at room temperature.

The oxidized CSF-1 dimer was found to be soluble in 1.2M ammonium sulfate. Further purification by hydrophobic interaction chromatography on a phenyl-Sepharose column as described in Example 5 may be performed.

Modifications of the above-described embodiments for carrying out the invention that are obvious to those of skill in the fields of biochemistry, especially protein purification and related fields, are intended to be within the scope of the following claims.

We claim:

1. A method to obtain purified, biologically active CSF-1 dimer from the product of a CSF-1 gene recombinantly expressed in bacteria, which method comprises:

(a) recovering in a chaotropic environment and under reducing conditions, the reduced monomeric, solubilized form of said CSF-1 product from bacterial cells;

(b) refolding, including formation of CSF-1 dimer, the monomer of (a) under refolding conditions; and (c) purifying the refolded, dimerized CSF-1 of (b).

2. The method of claim 1 wherein the reduced monomer of (a) is recovered in the presence of a reducing agent capable of reducing disulfide linkages to sulfhydral groups.

3. The method of claim 1 wherein the product of CSF-1 gene expression is an insoluble monomeric CSF-1 protein and wherein the method further includes the step of isolating insoluble protein containing CSF-1 monomer and solubilizing the insoluble protein to obtain the monomeric CSF-1 of (a).

4. The method of claim 1 which further includes the step of purifying the reduced monomeric form of (a) by a process selected from the group consisting of:

(i) sizing gel chromatography;

(ii) ion-exchange chromatography; and (iii) hydrophobic interaction chromatography.

5. The method of claim 4 wherein the product of CSF-1 gene expression is an insoluble monomeric CSF-1 protein and wherein the method further includes the step of isolating insoluble protein containing CSF-1 monomer and solubilizing the insoluble protein to obtain the monomeric CSF-1 of (a).

6. The method of claim 4 wherein the refolding conditions of (b) comprise dilution of the chaotropic environment wherein disulfide bonds are formed through air oxidation.

7. The method of claim 1 wherein the chaotropic environment is selected from 2–8M guanidinium ion and 4–8M urea.

8. The method of claim 7 wherein the chaotropic environment is about 7M guanidinium ion.

9. The method of claim 7 wherein the chaotropic environment is about 8M urea.

10. The method of claim 2 wherein the reducing agent is a thiol compound.

11. The method of claim 10 wherein the thiol is DTT.

12. The method of claim 1 wherein the refolding conditions of (b) comprise dilution of the chaotropic environment in the presence of a redox system.

13. The method of claim 1 wherein the refolding conditions of (b) comprise dilution of the chaotropic environment in the presence of a sulfitolysis reagent.

14. The method of claim 12 wherein the method further includes the step of diafiltration to remove the redox system prior to the purification step (c).

15. The method of claim 12 wherein the method further includes treating with a divalent metal cation to promote disulfide bond formation.

16. The method of claim 15 wherein the divalent metal cation is generated by the addition of cupric chloride.

17. The method of claim 1 wherein the dimeric form of (c) is purified by one or more of the processes selected from the group consisting of:

(i) sizing gel chromatography;

(ii) ion-exchange chromatography;

(iii) affinity chromatography; and (iv) hydrophobic interaction chromatography.

18. The method of claim 17 wherein the process is ion-exchange chromatography.

19. The method of claim 18 wherein the ion-exchange chromatography utilizes DEAE Sepharose chromatography.

20. The method of claim 19 wherein the DEAE Sepharose chromatography is performed at about pH 5.5 to about pH 7.0.

21. The method of claim 20 wherein the pH is 6.5.

22. The method of claim 19 wherein the protein is further purified by hydrophobic interaction chromatography.

23. The method of claim 22 wherein the hydrophobic interaction chromatography utilizes phenyl-Sepharose or phenyl-TSK.

24. The method of claim 17 wherein the process is hydrophobic interaction chromatography.

25. The method of claim 24 wherein the hydrophobic interaction chromatography utilizes phenyl-Sepharose or phenyl-TSK.

26. The method of claim 3 wherein said solubilizing employs treating with a chaotropic environment in the presence of a reducing agent.

27. The method of claim 26 wherein the chaotropic environment is 2–8M guanidinium salt and the reducing agent is a thiol.

28. The method of claim 27 wherein the thiol is DTT.

29. The method of claim 26 wherein the chaotropic environment is 4–8M urea and the reducing agent is a thiol.

30. The method of claim 3 wherein expression is under control of the lambda phage $P_L$ promoter.

31. The method of claim 1 which further comprises the step of separating any insoluble aggregates formed from the CSF-1 protein under the refolding conditions of (b), solubilizing said aggregates, and subjecting said solubilized aggregates to refolding conditions to increase the yield of said CSF-1 dimer.

32. The method of claim 1 wherein the CSF-1 is the expression product of gene constructs selected from the group consisting of: asp$_{59}$SCSF/C∇150 and the corresponding N∇2 or N∇3 analogs thereof; asp$_{59}$SCSF/C∇158 and the corresponding N∇73 analog thereof; LCSF/C∇190; ser$_{157}$LCSF/C∇221, ser$_{159}$LCSF/C∇221, ser$_{157}$ser$_{159}$LCSF/C∇221 and the corresponding N∇2 or N∇3 analogs thereof; and LCSF/C∇221 and the corresponding N∇3 analog thereof.

33. The method of claim 1 wherein the CSF-1 is the expression product of constructs selected from the group consisting of: asp$_{59}$SCSF and the N∇2 or N∇3 analogs thereof; asp$_{59}$SCSF/C∇158 and the corresponding N∇2 analog thereof; LCSF, LCSF/C∇150, LCSF/C∇190, ser$_{157}$ser$_{159}$LCSF/C∇221, ser$_{157}$ser$_{159}$LCSF/C∇223, and the corresponding N∇2 or N∇3 analogs thereof; LCSF/C∇221 and the corresponding N∇2 analog thereof.

34. A method for obtaining purified dimeric CSF-1 which comprises separating insoluble aggregates formed from CSF-1 under refolding conditions, solubilizing said aggregates, and subjecting said solubilized aggregates to refolding conditions.

35. A method to obtain a CSF-1 heterodimer, which method comprises subjecting a mixture of at least two solubilized CSF-1 monomers having different primary sequences produced by expression in bacteria to refolding conditions.

36. The method of claim 35 which further includes purification of the heterodimer from refolded CSF-1 homodimers.

37. The method of claim 35 wherein the mixture of CSF-1 monomers having different primary sequences and obtained by expression in different recombinant cells is obtained by mixing in vitro.

38. The method of claim 35 wherein the mixture of CSF-1 monomers having different primary sequences is obtained by expressing DNA constructs encoding at least two different CSF-1 primary sequences in the same host.

39. A method to prepare clinically pure, biologically active refolded CSF-1 dimer having an endotoxin content of less than 1.0 ng/mg of CSF and substantially free of pyrogens which process comprises subjecting a preparation containing biologically active CSF-1 dimer prepared from CSF-1 produced recombinantly in bacteria to chromatography using a hydrophobic interaction column.

40. The method of claim 39 wherein the hydrophobic interaction column is selected from phenyl-Sepharose and phenyl-TSK.

41. The method of claim 1 wherein the CSF-1 gene encodes LCSF/N∇3C∇221, asp$_{59}$SCSF/N∇3C∇150, asp$_{59}$SCSF/N∇3C∇158, ser$_{157}$LCSF/N∇3C∇221, ser$_{159}$LCSF/N∇3C∇221, or ser$_{157}$ser$_{159}$LCSF/N∇3C∇221.

* * * * *

UNITED STATES PATENT AND TRADEMARK OFFICE

CERTIFICATE OF CORRECTION

PATENT NO. : 4,929,700
DATED : May 29, 1990
INVENTOR(S) : Robert Halenbeck, *et al.*

It is certified that error appears in the above-indentified patent and that said Letters Patent is hereby corrected as shown below:

At column 18, line 39, please delete "Chromatocraphy" and replace therefore --Chromatography--.

At column 21, line 41, please delete "sonciation" and replace therefore --sonication--.

Signed and Sealed this

Twenty-seventh Day of January, 1998

Attest:

BRUCE LEHMAN

*Attesting Officer*

*Commissioner of Patents and Trademarks*